(12) United States Patent
Pawlowski et al.

(10) Patent No.: US 12,241,131 B2
(45) Date of Patent: Mar. 4, 2025

(54) METHODS AND SYSTEMS OF MULTI-ASSAY PROCESSING AND ANALYSIS

(71) Applicant: Abbott Molecular Inc., Des Plaines, IL (US)

(72) Inventors: Frank Pawlowski, Amherst, NH (US); Joseph P. Skinner, Libertyville, IL (US); Jack Kessler, Southborough, MA (US); Sonal Sadaria Nana, Chicago, IL (US)

(73) Assignee: Abbott Molecular Inc., Des Plaines, IL (US)

( * ) Notice: Subject to any disclaimer, the term of this patent is extended or adjusted under 35 U.S.C. 154(b) by 887 days.

(21) Appl. No.: 17/390,591

(22) Filed: Jul. 30, 2021

(65) Prior Publication Data

US 2022/0010387 A1    Jan. 13, 2022

Related U.S. Application Data

(63) Continuation of application No. 15/459,666, filed on Mar. 15, 2017, now Pat. No. 11,104,962.

(Continued)

(51) Int. Cl.
*C12Q 1/6888* (2018.01)
*B01L 9/00* (2006.01)
(Continued)

(52) U.S. Cl.
CPC ............ *C12Q 1/6888* (2013.01); *B01L 9/523* (2013.01); *C12Q 1/6806* (2013.01); *G01N 30/88* (2013.01);
(Continued)

(58) Field of Classification Search
CPC ..... B01L 9/523; C12Q 1/6806; C12Q 1/6888; C12Q 2527/113; C12Q 2531/113;
(Continued)

(56) References Cited

U.S. PATENT DOCUMENTS 9,046,455 B2    6/2015   Wilson et al.
2007/0116600 A1  5/2007   Kochar
(Continued)

FOREIGN PATENT DOCUMENTS

CN    101068932    5/2006
CN    102224408    4/2010
(Continued)

OTHER PUBLICATIONS

Aetna PCR selected indications policy bulletin (2020).
(Continued)

*Primary Examiner* — Jennifer Wecker
(74) *Attorney, Agent, or Firm* — Edward J. Baba; Mandar A. Joshi; Bozicevic, Field & Francis LLP

(57) ABSTRACT

The instant disclosure provides methods of multi-assay processing and multi-assay analysis. Such multi-assay processing and analysis pertain to automated detection of target nucleic acids, e.g., as performed in the clinical setting for diagnostic purposes. Also provided are common assay timing protocols derived from a variety of individual nucleic acid amplification and analysis protocols and modified to prevent resource contention. The instant disclosure also provides systems and devices for practicing the methods as described herein.

28 Claims, 6 Drawing Sheets

Related U.S. Application Data

(60) Provisional application No. 62/308,625, filed on Mar. 15, 2016.

(51) Int. Cl.
| | |
|---|---|
| *C12Q 1/6806* | (2018.01) |
| *G01N 30/88* | (2006.01) |
| *G01N 33/48* | (2006.01) |
| *G01N 35/00* | (2006.01) |
| *G01N 33/569* | (2006.01) |

(52) U.S. Cl.
CPC ....... *G01N 33/48* (2013.01); *G01N 35/00584* (2013.01); *G01N 33/56983* (2013.01); *G01N 35/00* (2013.01); *G01N 2035/00326* (2013.01)

(58) Field of Classification Search
CPC ........ C12Q 2545/114; C12Q 2561/113; G01N 2035/00326; G01N 30/88; G01N 33/48; G01N 33/56983; G01N 35/00; G01N 35/00584; Y02A 50/30
See application file for complete search history.

(56) References Cited

U.S. PATENT DOCUMENTS

| | | |
|---|---|---|
| 2012/0329664 A1 | 12/2012 | Saxonov et al. |
| 2015/0346228 A1 | 12/2015 | Maeda et al. |
| 2017/0269114 A1* | 9/2017 | Bryant ............... G01N 35/0099 |
| 2018/0230552 A1 | 8/2018 | Goletz et al. |

FOREIGN PATENT DOCUMENTS

| | | |
|---|---|---|
| CN | 103103106 | 5/2013 |
| JP | 2014-509865 | 4/2014 |
| JP | 2014-128201 | 7/2014 |
| WO | 03091710 | 11/2003 |
| WO | 2004074847 | 9/2004 |
| WO | 2009009419 | 1/2009 |
| WO | 2012012779 | 1/2012 |
| WO | 2012092259 | 7/2012 |
| WO | 2012142516 | 10/2012 |
| WO | 2015013688 | 1/2015 |
| WO | 2015150278 | 10/2015 |
| WO | 2017160980 | 9/2017 |
| WO | 2017161046 | 9/2017 |
| WO | 2017161053 | 9/2017 |
| WO | 2017161056 | 9/2017 |
| WO | 2017161058 | 9/2017 |

OTHER PUBLICATIONS

Giokas et al. (2014) "Title?" Analytical Chemistry 86: 6202-6207.
Grissom et al. (2012) "Path Scheduling on Digital Microfluidic Biochips" Design Automation Conference (DAC), 2012 49th ACM/ECAC/IEEE, IEEE, 26-35.
Grissom et al. (2012) DAC '12 Proceedings of the 49th Annual Design Automation Conference, pp. 26.

* cited by examiner

FIG. 3

Step 1, 3, 5 Uses Resource 1
Step 2 and 4 use resource 2 and 4 respectively

Unlimited Resource Case

Limited Resources with Resource Contention

Contentions Eliminated

FIG. 4

METHODS AND SYSTEMS OF MULTI-ASSAY PROCESSING AND ANALYSIS

CROSS-REFERENCE TO RELATED APPLICATIONS

This application is a continuation of U.S. patent application Ser. No. 15/459,666, filed Mar. 15, 2017, issued as U.S. Pat. No. 11,104,962, which claims priority to the filing date of the U.S. Provisional Patent Application Ser. No. 62/308,625, filed Mar. 15, 2016, the disclosure of which application is herein incorporated by reference.

BACKGROUND

Molecular diagnostic assays, including nucleic acid amplification based methods, have become a mainstay of clinical medicine and the variety of available tests and the demand for such tests by clinicians has increased dramatically. This demand places increasing pressures on clinical laboratories to process, not only a greater volume of samples, but also a greater diversity of tests on the samples. Thus, there is a burden on clinical testing facilities to efficiently perform a wider range of different nucleic acid amplification based tests.

Assay protocols define all the reagents, processing steps, processing times, temperature profiles, etc., required to process a sample through an automated instrument in order to obtain a diagnostic result. Historically, unique assay protocols containing varying reagents, steps and times are developed for each type of assay in order to optimize assay performance. For instruments that process samples in batch mode, where only one type of assay is processed per run, having unique assay protocols does not impact the overall system throughput and scheduling complexity since the protocol is the same for all samples being run in the batch. However, in the case of instruments that process multiple assay types simultaneously per run, unique assay protocols have a significant impact on the scheduler complexity and efficient use of system resources.

SUMMARY

Aspects of the instant disclosure include methods for multi-assay processing and multi-assay quantification and multi-assay processing systems.

Aspects of the instant disclosure include a method of multi-assay processing that includes: a) preparing a sample processing unit (SPU) cartridge for each of two or more different target nucleic acid detection assays; b) loading a sample into each prepared SPU cartridge; c) processing each loaded SPU cartridge to isolate a sample nucleic acid for each of the two or more different target nucleic acid detection assays; and d) amplifying and analyzing each sample nucleic acid for a target nucleic acid specific to each of the two or more different target nucleic acid detection assays, wherein the method comprises at least one delay step within or between steps a) through d) and steps a) through d) are each performed for a time period that is equal for the two or more different target nucleic acid detection assays. In some instances, aspects of the method include a delay step between steps a) and b), a delay step between steps b) and c) and/or a delay step between steps c) and d).

In some instances, aspects of the method include rehydrating lyophilized reagents for each of the two or more different target nucleic acid detection assays prior to the preparing, wherein the rehydrating is performed for a time period that is equal for the two or more different target nucleic acid detection assays. In some instances, aspects of the method include a delay step following the rehydrating.

In some instances, aspects of the method include pre-treating each loaded SPU cartridge prior to the processing, wherein the pre-treating is performed for a time period that is equal for the two or more different target nucleic acid detection assays. In some instances, aspects of the method include a delay step following the pre-treating.

In some instances, aspects of the method include where the pre-treating comprises contacting the sample with a protease.

In some instances, aspects of the method include where the processing comprises transferring the sample into a solution comprising a lysis buffer, wherein the transferring is performed for a time period that is equal for the two or more different target nucleic acid detection assays. In some instances, aspects of the method include a delay step following the transferring.

In some instances, aspects of the method include where the processing comprises eluting the nucleic acid and transferring the eluted nucleic acid into a reaction vessel for the amplifying and analyzing, wherein the eluting is performed for a time period that is equal for the two or more different target nucleic acid detection assays. In some instances, aspects of the method include a delay step following the eluting.

In some instances, aspects of the method include where two or more different target nucleic acid detection assays include an assay to detect a human immunodeficiency virus (HIV) nucleic acid, an assay to detect a hepatitis C virus (HCV) nucleic acid, an assay to detect a hepatitis B virus (HBV) nucleic acid, an assay to detect a *Chlamydia trachomatis* (CT) nucleic acid, a *Neisseria gonorrhoeae* (NG) nucleic acid or a combination there of, an assay to detect a Human papillomavirus (HPV) nucleic acid, an assay to detect a Cytomegalovirus (CMV) nucleic acid, an assay to detect an Epstein-Barr virus (EBV) nucleic acid, an assay to detect a BK virus nucleic acid, an assay to detect a Methicillin-resistant *Staphylococcus aureus* (MRSA) nucleic acid, an assay to detect a *Clostridium difficile* (D. Diff.) nucleic acid, an assay to detect a Vancomycin-resistant *Enterococcus* (VRE) nucleic acid, an assay to detect an Adenovirus nucleic acid, an assay to detect a tuberculosis (TB) nucleic acid, an assay to detect a Varicella-zoster virus (VZV) nucleic acid, an assay to detect a Herpes simplex virus (HSV) nucleic acid, an assay to detect a JC virus nucleic acid, an assay to detect an Enterovirus nucleic acid, an assay to detect a *Lymphogranuloma venereum* (LGV) nucleic acid, an assay to detect a Respiratory Viral Panel (RVP) nucleic acid, an assay to detect a human herpesvirus 6 (HHV6) nucleic acid, an assay to detect a *Trichomonas* (Trich) nucleic acid, a *Mycoplasma* (Myco) nucleic acid or a combination thereof, and/or an assay to detect a Norovirus nucleic acid. In some instances, aspects of the method include processing 3 or more different target nucleic acid detection assays. In some instances, aspects of the method include processing 10 or more different target nucleic acid detection assays.

Aspects of the instant disclosure include a method of multi-assay quantification that includes: a) initiating a nucleic acid amplification protocol in a first sample pair; b) scanning the first sample pair with an optical detector at a regular interval during the nucleic acid amplification protocol, wherein the interval allows for the collection of data by the optical detector at timepoints of the amplification protocol sufficient for quantification of the nucleic acid amplification in the first sample pair; c) initiating the nucleic acid amplification protocol in a second sample pair at a time that allows the second sample pair to be scanned by the optical detector at the regular intervals and collection of data by the optical detector at timepoints of the amplification protocol sufficient for quantification of nucleic acid amplification in the second sample pair.

In some instances, aspects of the multi-assay quantification method include initiating the nucleic acid amplification protocol of the first sample pair and initiating the nucleic acid amplification protocol of the second sample pair at essentially the same time. In some instances, aspects of the multi-assay quantification method include initiating the nucleic acid amplification protocol of the first sample pair and initiating the nucleic acid amplification protocol of the second sample pair at different times. In some instances, aspects of the multi-assay quantification method include where the scanning is performed three or more times during the nucleic acid amplification protocol. In some instances, aspects of the multi-assay quantification method include where the interval allows for the collection of data by the optical detector at more timepoints of the amplification protocol than necessary for quantification of the nucleic acid amplification in the first and second sample pairs.

In some instances, aspects of the multi-assay quantification method include initiating the nucleic acid amplification protocol in a third sample pair at a time that allows the third pair to be scanned by the optical detector at the regular intervals and collection of data by the optical detector at timepoints of the amplification protocol sufficient for quantification of nucleic acid amplification in the third sample pair. In some instances, aspects of the multi-assay quantification method include initiating the nucleic acid amplification protocol of the first, second and third sample pairs at essentially the same time. In some instances, aspects of the multi-assay quantification method include initiating of the nucleic acid amplification protocol of the first, second and third sample pairs at different times.

In some instances, aspects of the multi-assay quantification method include initiating the nucleic acid amplification protocol in a fourth sample pair at a time that allows the fourth pair to be scanned by the optical detector at the regular intervals and collection of data by the optical detector at timepoints of the amplification protocol sufficient for quantification of nucleic acid amplification in the fourth sample pair. In some instances, aspects of the multi-assay quantification method include initiating of the nucleic acid amplification protocol of the first, second, third and fourth sample pairs at essentially the same time. In some instances, aspects of the multi-assay quantification method include initiating of the nucleic acid amplification protocol of the first, second, third and fourth sample pairs at different times.

In some instances, aspects of the multi-assay quantification method include initiating the nucleic acid amplification protocol in a fifth sample pair at a time that allows the fifth pair to be scanned by the optical detector at the regular intervals and collection of data by the optical detector at timepoints of the amplification protocol sufficient for quantification of nucleic acid amplification in the fifth sample pair. In some instances, aspects of the multi-assay quantification method include initiating of the nucleic acid amplification protocol of the first, second, third, fourth and fifth sample pairs at essentially the same time. In some instances, aspects of the multi-assay quantification method include initiating of the nucleic acid amplification protocol of the first, second, third, fourth and fifth sample pairs at different times.

In some instances, aspects of the multi-assay quantification method include initiating the nucleic acid amplification protocol in a sixth sample pair at a time that allows the sixth pair to be scanned by the optical detector at the regular intervals and collection of data by the optical detector at timepoints of the amplification protocol sufficient for quantification of nucleic acid amplification in the sixth sample pair. In some instances, aspects of the multi-assay quantification method include initiating of the nucleic acid amplification protocol of the first, second, third, fourth, fifth and sixth sample pairs at essentially the same time. In some instances, aspects of the multi-assay quantification method include the initiating of the nucleic acid amplification protocol of the first, second, third, fourth, fifth and sixth sample pairs at different times.

Aspects of the instant disclosure include a multi-assay processing system including: a) a sample processing unit (SPU) cartridge preparation module; b) a sample loading module; c) a SPU processing module; d) a nucleic acid amplification and analysis module; and e) control circuitry configured to perform a method as herein described.

In some instances, aspects of the system include a module for rehydrating lyophilized reagents. In some instances, aspects of the system include an SPU processing module configured for pre-treating each sample prior to processing the sample. In some instances, aspects of the system include a reaction transfer module. In some instances, aspects of the system include a single robotic pipette resource that functions in the SPU cartridge preparation module. In some instances, aspects of the system include where the single robotic pipette resource also functions in the sample loading module, the module for rehydrating lyophilized reagents and/or the reaction transfer module. In some instances, aspects of the system include one or more bulk filling robots. In some instances, aspects of the system include a single bulk filling robot.

In some instances, aspects of the system include one or more waste robots. In some instances, aspects of the system include a single waste robot. In some instances, aspects of the system include one or more SPU cartridge handling robots. In some instances, aspects of the system include a single SPU cartridge handling robot.

BRIEF DESCRIPTION OF THE FIGURES

FIG. 3 demonstrates a sequence with appropriately placed timing gaps (i.e., delays) resulting in a fixed cadence of sample input that allows for a single lockstep timing protocol in a system with finite resources.

FIG. 4 demonstrates how three different assays, each with four samples, can be configured during amplification and detection for coordinated measurements according to an embodiment of the disclosure.

DEFINITIONS

Figure 1:
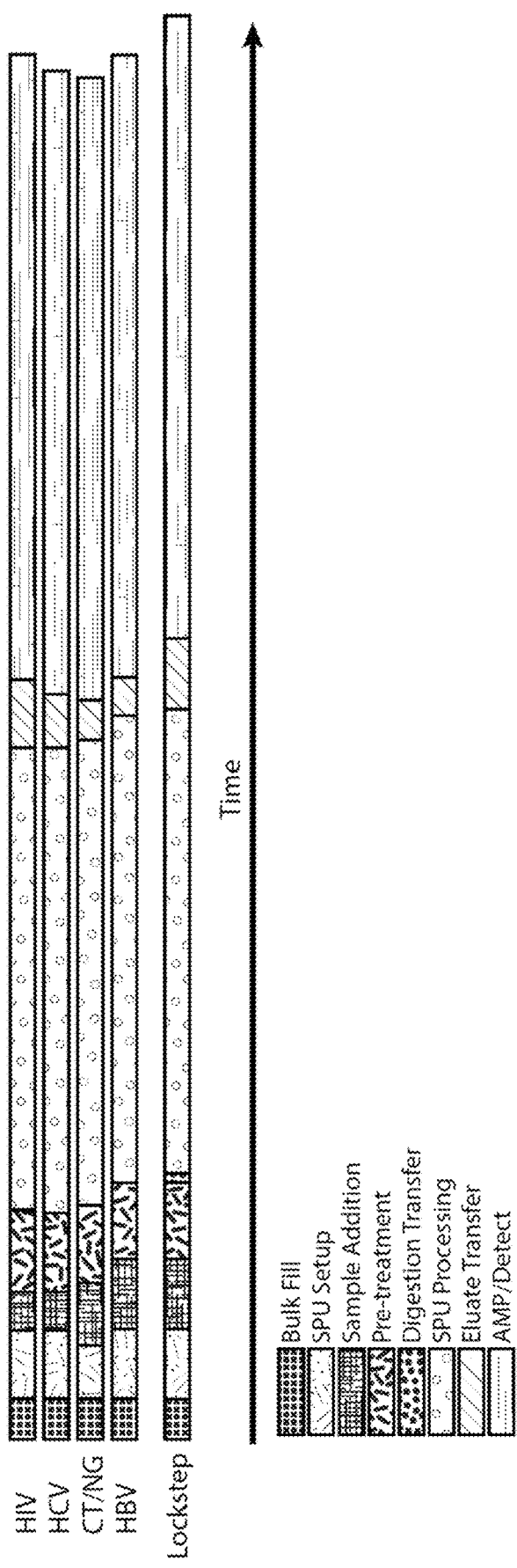
FIG. 1 provides an idealized lockstep protocol used to harmonize the processing of samples for different nucleic acid assays related to HIV, HCV, CT/NG and HBV diagnostic protocols.

The term "analyte" as used herein an analyte refers to a target molecule to be detected in a sample wherein detection of the analyte may be indicative of a biological state of the organism from which the sample was derived. For example, where an analyte is a nucleic acid analyte, detection of the nucleic acid analyte may be indicative of a biological state of the organisms from which the sample was derived including e.g., where detection of viral nucleic acid may indicate infection with a particular pathogen, etc.

The term "reaction vessel" as used herein generally referrers to a container within which an amplification reaction is performed. Such reaction vessels may be obtained from commercial sources, e.g., as off-the-shelf components, or may be custom manufactured. Reaction vessels useful in nucleic acid amplification reactions will generally be capable of rapidly transferring heat across the vessel, e.g., through the use of highly conductive materials (e.g., thermally conductive plastics) or physical modifications of the vessel (e.g., thin walls). Common reaction vessels include but are not limited to e.g., tubes, vials, multi-well plates, and the like. Reaction vessels may be constructed of a variety of materials including but not limited to e.g., polymeric materials. In some instances, a method as described herein may be configured for use with a reaction vessel and/or reaction vessel system as described in U.S. Ser. No. 62/308,620, the disclosures of which are incorporated herein by reference in their entireties.

The term "assessing" includes any form of measurement, and includes determining if an element is present or not. The terms "determining", "measuring", "evaluating", "assessing" and "assaying" are used interchangeably and include quantitative and qualitative determinations. Assessing may be relative or absolute. "Assessing the identity of" includes determining the most likely identity of a particular compound or formulation or substance, and/or determining whether a predicted compound or formulation or substance is present or absent. "Assessing the quality of" includes making a qualitative or quantitative assessment of quality e.g., through the comparisons of a determined value to a reference or standard of known quality.

The term "bodily fluid" as used herein generally refers to fluids derived from a "biological sample" which encompasses a variety of sample types obtained from an individual or a population of individuals and can be used in a diagnostic, monitoring or screening assay. The definition encompasses blood and other liquid samples of biological origin. The definition also includes samples that have been manipulated in any way after their procurement, such as by mixing or pooling of individual samples, treatment with reagents, solubilization, or enrichment for certain components, such as nucleated cells, non-nucleated cells, pathogens, etc.

The term "biological sample" encompasses a clinical sample, and also includes cells in culture, cell supernatants, cell lysates, serum, plasma, biological fluid, and tissue samples. The term "biological sample" includes urine, saliva, cerebrospinal fluid, interstitial fluid, ocular fluid, synovial fluid, blood fractions such as plasma and serum, and the like.

The terms "control", "control assay", "control sample" and the like, refer to a sample, test, or other portion of an experimental or diagnostic procedure or experimental design for which an expected result is known with high certainty, e.g., in order to indicate whether the results obtained from associated experimental samples are reliable, indicate to what degree of confidence associated experimental results indicate a true result, and/or to allow for the calibration of experimental results. For example, in some instances, a control may be a "negative control" assay such that an essential component of the assay is excluded such that an experimenter may have high certainty that the negative control assay will not produce a positive result. In some instances, a control may be "positive control" such that all components of a particular assay are characterized and known, when combined, to produce a particular result in the assay being performed such that an experimenter may have high certainty that the positive control assay will not produce a positive result. Controls may also include "blank" samples, "standard" samples (e.g., "gold standard" samples), validated samples, etc.

By "control circuitry" or "data processing unit", as used herein, is meant any hardware and/or software combination that will perform the functions required of it. For example, any data processing unit herein may be a programmable digital microprocessor such as available in the form of an electronic controller, mainframe, server or personal computer (desktop or portable). Where the data processing unit is programmable, suitable programming can be communicated from a remote location to the data processing unit, or previously saved in a computer program product (such as a portable or fixed computer readable storage medium, whether magnetic, optical or solid state device based). In some instances, control circuitry or a data processing unit of the present disclosure may be specifically programmed to perform the functions required of it and may thus be referred to as a special purpose computer.

By "lockstep" or "lockstep protocol" is meant a protocol where the steps of the protocol follow one another as closely as possible. In some instances described herein a lockstep protocol may be determined based on corresponding steps of different protocols where such protocols will be performed in parallel or concomitantly. Thus, a lockstep protocol need not consist of only successive shortest steps of a particular protocol but may instead include one or more longest steps of various protocols that are to be performed in parallel.

By "cadence" is meant batch per unit time and, as it relates to a lockstep protocol, a cadence may relate to a regular or fixed point or time of sample input or sample processing initiation. Accordingly, a regular cadence may refer to the initiation of a batch at regular time intervals.

By "resource contention", as used herein, is meant a conflict over access to a shared resource of an integrated system. Resource contention may apply to the physical components of a system where such components are limiting to progression of a process. For example, where two modules of a system utilize a shared resource such resource may be in contention if/when both modules require the resource simultaneously.

By "batch", as used herein, is meant a grouping of common samples or assays processed in parallel according to a single protocol having a common initiation time. Samples or assays within batches of the instant disclosure may or may not be processed exactly alike but will generally initiate and terminate together. For example, samples and assays of the batch may be processed exactly alike throughout the entire protocol including e.g., where sample preparation, processing and amplification/analysis are identical for all samples or assays of the batch. In other instances, samples and assays of the batch may not be processed exactly alike throughout the entire protocol including e.g., where one or more of sample preparation, processing and/or amplification/analysis are not identical for all samples or assays of the batch.

DETAILED DESCRIPTION

The instant disclosure provides methods of multi-assay processing and multi-assay analysis. Such multi-assay processing and analysis pertain to automated detection of target nucleic acids, e.g., as performed in the clinical setting for diagnostic purposes. Also provided are common assay timing protocols derived from a variety of individual nucleic acid amplification and analysis protocols and modified to prevent resource contention. The instant disclosure also provides systems and devices for practicing the methods as described herein.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Methods

The instant disclosure provides methods of multi-assay processing where by "multi-assay" is meant multiple, two or more, different assays. Multi-assay processing and/or analysis may be performed by a single molecular analysis device including those molecular analysis devices having limited physical resources. In many embodiments, the instant methods pertain to multi-assay processing of nucleic acid amplification and analysis assays including but not limited to e.g., those involving PCR methods, including e.g., real-time PCR methods.

The PCR process is a nucleic acid amplification method whereby a target nucleic acid sequence is amplified by a factor of $2^n$ by repeating (1) a denaturing temperature (e.g., of 95° C.) that serves to denature the two strands of a double stranded nucleic acid template; (2) an annealing temperature (e.g., on the order of 55° C. to 65° C.) that serves to anneal one or more complementary nucleic acids to a single strand of the denatured nucleic acid; and (3) an extension temperature that provides the permissive temperature for a nucleic acid polymerase to extend the complementary nucleic acid according to the sequence of the template, alternately n times (referred as a "thermal cycle").

In real-time PCR, the amount of nucleic acid is measured at a plurality of time points during the amplification reaction to determine the actual or relative amount of target nucleic acid analyte initially present in the sample. Real-time PCR may be quantitative, semi-quantitative or qualitative. Real-time PCR is generally carried out in a thermal cycler with the capacity to illuminate each amplification sample with a beam of light of at least one specified wavelength and detect the fluorescence emitted by an excited fluorophore that is either incorporated into the amplicon or unquenched during amplification. Non-specific fluorochromes (e.g., DNA binding dyes such as e.g., SYBR Green) or specific fluorescent hybridization probes may be used. Using different-colored labels, fluorescent probes can be used in multiplex assays for monitoring several target sequences in the same tube.

One method of using fluorescently labeled probes relies on a DNA-based probe with a fluorescent reporter at one end and a quencher of fluorescence at the opposite end of the probe. The close proximity of the reporter to the quencher prevents detection of its fluorescence. When bound to a target sequence, breakdown of the probe by the 5' to 3' exonuclease activity of the polymerase breaks the reporter-quencher proximity and thus allows unquenched emission of fluorescence, which can be detected after excitation with a particular wavelength of light. An increase in the product targeted by the reporter probe at each PCR cycle therefore causes a proportional increase in fluorescence due to the breakdown of the probe and release of the reporter. Any convenient polymerase with 5' to 3' exonuclease activity may find use in such assays including but not limited to wild-type Taq polymerase and modified or engineered polymerases including but not limited to e.g., those available from commercial suppliers such as e.g., New England Biolabs (Ipswich, MA), Life Technologies (Carlsbad, CA), Sigma Aldrich (St. Louis, MO) and Kapa Biosystems, Inc. (Wilmington, MA) such as e.g., KAPA2G DNA Polymerases.

Various real-time PCR assays find use in clinical diagnostics including detection of a target nucleic acid of an infectious agent. As used herein an "infectious agent" includes any biological pathogen that may infect a host, where such pathogens have a nucleic acid component, e.g., a nucleic acid genome, that may be detected, referred to herein as a "target nucleic acid" in an assay as described herein. As such infectious agents of the instant disclosure will vary and may include but are not limited to e.g., parasites, bacteria, yeast, fungi, viruses, and the like. The instant methods and systems may be applied to any infectious agent having a nucleic acid component that may be detected by PCR methods, including real-time PCR and reverse transcription (RT) PCR, including real-time RT-PCR. As such, a target nucleic acid of an infectious agent may be DNA or RNA, including but not limited to e.g., single stranded DNA, double stranded DNA, single stranded RNA, double stranded RNA, and the like.

Multi-assay methods and systems find use in automated detection of target nucleic acids for a plurality of different assays, including multiple different clinically relevant nucleic acid detection assays. In some instances, multi-assay methods may apply multiple different assays to a single biological sample including e.g., where a single sample is divided into aliquots and each aliquot is applied to two or more different nucleic acid detection assays. In some instances, multi-assay methods may apply multiple different assays to different biological samples including e.g., where different biological samples may be derived from different tissues of a single subject, derived from the subject at different times, derived from different subjects, etc.

In some instances, the methods and systems as described herein involve simultaneous or co-timely or overlapping detection of a plurality of target nucleic acids derived from an organism. Organisms from which target nucleic acids may be derived include clinically relevant and non-clinically relevant organisms. Non-clinically relevant organisms may include e.g., organisms useful in research applications, organisms useful in industrial applications, organisms useful in agricultural applications, organisms of environmental concern, etc.

In some instances, a multi-assay processing, analysis or detection method may find use in simultaneous or co-timely or overlapping processing, analysis or detection of a plurality of clinically relevant target nucleic acids including but not limited to e.g., target nucleic acids derived or originating from one or more clinically relevant pathogens such as e.g., *Acinetobacter baumannii, Acinetobacter lwoffii, Acinetobacter* spp. (incl. MDR), Actinomycetes, Adenovirus, *Aeromonas* spp., *Alcaligenes faecalis, Alcaligenes* spp./*Achromobacter* spp., *Alcaligenes xylosoxidans* (incl. ESBL/MRGN), Arbovirus, *Aspergillus* spp., Astrovirus, *Bacillus anthracis, Bacillus cereus, Bacillus subtilis, Bacteroides fragilis, Bartonella quintana, Bordetella pertussis, Borrelia burgdorferi, Borrelia recurrentis, Brevundimonas diminuta, Brevundimonas vesicularis, Brucella* spp., *Burkholderia cepacia* (incl. MDR), *Burkholderia mallei, Burkholderia pseudomallei, Campylobacter jejuni/coli, Candida albicans, Candida krusei, Candida parapsilosis*, Chikungunya virus (CHIKV), *Chlamydia pneumoniae, Chlamydia psittaci, Chlamydia trachomatis, Citrobacter* spp., *Clostridium botulinum, Clostridium difficile, Clostridium perfringens, Clostridium tetani*, Coronavirus (incl. SARS- and MERS-CoV), *Corynebacterium diphtheriae, Corynebacterium pseudotuberculosis, Corynebacterium* spp., *Corynebacterium ulcerans, Coxiella burnetii*, Coxsackievirus, Crimean-Congo haemorrhagic fever virus, *Cryptococcus neoformans, Cryptosporidium hominis, Cryptosporidium parvum, Cyclospora cayetanensis*, Cytomegalovirus (CMV), Dengue virus, Ebola virus, Echovirus, *Entamoeba histolytica, Enterobacter aerogenes, Enterobacter cloacae*(incl. ESBL/MRGN), *Enterococcus faecalis* (incl. VRE), *Enterococcus faecium* (incl. VRE), *Enterococcus hirae, Epidermophyton* spp., Epstein-Barr virus (EBV), *Escherichia coli* (incl. EHEC, EPEC, ETEC, EIEC, EAEC, ESBL/MRGN, DAEC), Foot-and-mouth disease virus (FMDV), *Francisella tularensis, Giardia lamblia, Haemophilus influenzae*, Hantavirus, *Helicobacter pylori*, Helminths (Worms), Hepatitis A virus (HAV), Hepatitis B virus (HBV), Hepatitis C virus (HCV), Hepatitis D virus, Hepatitis E virus, Herpes simplex virus (HSV), *Histoplasma capsulatum*, Human enterovirus 71, Human herpesvirus 6 (HHV-6), Human herpesvirus 7 (HHV-7), Human herpesvirus 8 (HHV-8), Human immunodeficiency virus (HIV), Human metapneumovirus, Human papillomavirus, Influenza virus, *Klebsiella granulomatis, Klebsiella oxytoca* (incl. ESBL/MRGN), *Klebsiella pneumoniae* MDR (incl. ESBL/MRGN), Lassa virus, *Leclercia adecarboxylata, Legionella pneumophila, Leishmania* spp., *Leptospira interrogans, Leuconostoc pseudomesenteroides, Listeria monocytogenes*, Marburg virus, Measles virus, *Micrococcus luteus, Microsporum* spp., Molluscipoxvirus, *Morganella* spp., Mumps virus, *Mycobacterium chimaera* Myco, *Mycobacterium leprae* Myco, *Mycobacterium tuberculosis* (incl. MDR), *Mycoplasma genitalium, Mycoplasma pneumoniae, Neisseria meningitidis, Neisseria gonorrhoeae*, Norovirus, *Orientia tsutsugamushi, Pantoea agglomerans*, Parainfluenza virus, Parvovirus, *Pediculus humanus* capitis, *Pediculus humanus* corporis, *Plasmodium* spp., *Pneumocystis jiroveci*, Poliovirus, Polyomavirus, *Proteus mirabilis*(incl. ESBL/MRGN), *Proteus vulgaris, Providencia rettgeri, Providencia stuartii, Pseudomonas aeruginosa, Pseudomonas* spp., Rabies virus, *Ralstonia* spp., Respiratory syncytial virus (RSV), Rhinovirus, *Rickettsia prowazekii, Rickettsia typhi, Roseomonas gilardii*, Rotavirus, Rubella virus, *Salmonella enteritidis, Salmonella paratyphi, Salmonella* spp., *Salmonella typhimurium, Sarcoptes scabiei* (Itch mite), Sapovirus, *Serratia marcescens* (incl. ESBL/MRGN), *Shigella sonnei, Sphingomonas species, Staphylococcus aureus*(incl. MRSA, VRSA), *Staphylococcus capitis, Staphylococcus epidermidis*(incl. MRSE), *Staphylococcus haemolyticus, Staphylococcus hominis, Staphylococcus lugdunensis, Staphylococcus saprophyticus, Stenotrophomonas maltophilia, Streptococcus pneumoniae, Streptococcus pyogenes* (incl. PRSP), *Streptococcus* spp., TBE virus, *Toxoplasma gondii, Treponema pallidum, Trichinella spiralis, Trichomonas vaginalis, Trichophyton* spp., *Trichosporon* spp., *Trypanosoma brucei gambiense, Trypanosoma brucei rhodesiense, Trypanosoma cruzi*, Vaccinia virus, Varicella zoster virus, Variola virus, *Vibrio cholerae*, West Nile virus (WNV), Yellow fever virus, *Yersinia enterocolitica, Yersinia pestis, Yersinia pseudotuberculosis*, Zika virus, and the like.

In some instances, a multi-assay processing, analysis or detection method may find use in simultaneous or co-timely or overlapping processing, analysis or detection of a plurality of clinically relevant target nucleic acids including but not limited to e.g., target nucleic acids derived or originating from one or more clinically relevant pathogenic bacteria such as e.g., *Bacillus anthracis, Bacillus cereus, Bartonella henselae, Bartonella quintana, Bordetella pertussis, Borrelia burgdorferi, Borrelia garinii, Borrelia afzelii, Borrelia recurrentis, Brucella abortus, Brucella canis, Brucella melitensis, Brucella suis, Campylobacter jejuni, Chlamydia pneumoniae, Chlamydia trachomatis, Chlamydophila psittaci, Clostridium botulinum, Clostridium difficile, Clostridium perfringens, Clostridium tetani, Corynebacterium diphtheriae, Enterococcus faecalis, Enterococcus faecium, Escherichia coli, Francisella tularensis, Haemophilus influenzae, Helicobacter pylori, Legionella pneumophila, Leptospira interrogans, Leptospira santarosai, Leptospira weilii, Leptospira noguchii, Listeria monocytogenes, Mycobacterium leprae, Mycobacterium tuberculosis, Mycobacterium ulcerans, Mycoplasma pneumoniae, Neisseria gonorrhoeae, Neisseria meningitidis, Pseudomonas aeruginosa, Rickettsia rickettsii, Salmonella typhi, Salmonella typhimurium, Shigella sonnei, Staphylococcus aureus, Staphylococcus epidermidis, Staphylococcus saprophyticus, Streptococcus agalactiae, Streptococcus pneumoniae, Streptococcus pyogenes, Treponema pallidum, Ureaplasma urealyticum, Vibrio cholerae, Yersinia pestis, Yersinia enterocolitica, Yersinia pseudotuberculosis*, etc.

In some instances, a multi-assay processing, analysis or detection method may find use in simultaneous or co-timely or overlapping processing, analysis or detection of a plurality of clinically relevant target nucleic acids including but not limited to e.g., target nucleic acids derived or originating from one or more clinically relevant pathogenic protozoans such as e.g., protozoan parasites including but not limited to e.g., *Acanthamoeba* spp., *Balamuthia mandrillaris, Babesia B. divergens, B. bigemina, B. equi, B. microfti, B. duncani, Balantidium coli, Blastocystis* spp., *Cryptosporidium* spp., *Cyclospora cayetanensis, Dientamoeba fragilis, Entamoeba histolytica, Giardia lamblia, Isospora belli, Leishmania* spp., *Plasmodium falciparum* (80% of cases), *Plasmodium vivax, Plasmodium ovale curtisi, Plasmodium ovale wallikeri, Plasmodium malariae, Plasmodium knowlesi, Rhinosporidium seeberi, Sarcocystis bovihominis, Sarcocystis suihominis, Toxoplasma gondii, Trichomonas vaginalis, Trypanosoma brucei, Trypanosoma cruzi*, etc.

In some instances, a multi-assay processing, analysis or detection method may find use in simultaneous or co-timely or overlapping processing, analysis or detection of a plurality of clinically relevant target nucleic acids including but not limited to e.g., target nucleic acids derived or originating from one or more clinically relevant pathogenic worms such as e.g., Helminths parasites including but not limited to e.g., Cestoda, *Taenia multiceps, Diphyllobothrium latum, Echinococcus granulosus, Echinococcus multilocularis, E. vogeli, E. oligarthrus, Taenia saginata, Taenia solium, Bertiella mucronata, Bertiella studeri, Spirometra erinaceieuropaei*, etc.

In some instances, a multi-assay processing, analysis or detection method may find use in simultaneous or co-timely or overlapping processing, analysis or detection of a plurality of clinically relevant target nucleic acids including but not limited to e.g., target nucleic acids derived or originating from one or more clinically relevant flukes including but not limited to e.g., *Clonorchis sinensis; Clonorchis viverrini, Dicrocoelium dendriticum, Metagonimus yokogawai, Metorchis conjunctus, Opisthorchis viverrini, Opisthorchis felineus, Clonorchis sinensis, Paragonimus westermani; Paragonimus africanus; Paragonimus caliensis; Paragonimus kellicotti; Paragonimus skrjabini; Paragonimus uterobilateralis, Schistosoma* sp., *Schistosoma mansoni* and *Schistosoma intercalatum, Schistosoma haematobium, Schistosoma japonicum, Schistosoma mekongi-, Echinostoma echinatum, Trichobilharzia regenti*, Schistosomatidae, etc.

In some instances, a multi-assay processing, analysis or detection method may find use in simultaneous or co-timely or overlapping processing, analysis or detection of a plurality of clinically relevant target nucleic acids including but not limited to e.g., target nucleic acids derived or originating from one or more clinically relevant roundworms including but not limited to e.g., *Ancylostoma duodenale, Necator americanus, Angiostrongylus costaricensis, Ascaris* sp. *Ascaris lumbricoides, Baylisascaris procyonis, Brugia malayi, Brugia timori, Dioctophyme renale, Dracunculus medinensis, Enterobius vermicularis, Enterobius gregorii, Halicephalobus gingivalis, Loa loa filaria, Mansonella streptocerca, Onchocerca volvulus, Strongyloides stercoralis, Thelazia californiensis, Thelazia callipaeda, Toxocara canis, Toxocara cati, Trichinella spiralis, Trichinella britovi, Trichinella nelsoni, Trichinella nativa, Trichuris trichiura, Trichuris vulpis, Wuchereria bancrofti*, etc.

In some instances, a multi-assay processing, analysis or detection method may find use in simultaneous or co-timely or overlapping processing, analysis or detection of a plurality of clinically relevant target nucleic acids including but not limited to e.g., target nucleic acids derived or originating from one or more relevant other parasites including but not limited to e.g., Archiacanthocephala, *Moniliformis moniliformis, Linguatula serrata, Oestroidea*, Calliphoridae, Sarcophagidae, *Tunga penetrans, Dermatobia hominis*, Acari, Cimicidae *Cimex lectularius, Pediculus humanus, Pediculus humanus corporis, Pthirus pubis, Demodex folliculorum/brevis/canis, Sarcoptes scabiei, Cochliomyia hominivorax, Pulex irritans*, Arachnida Ixodidae and Argasidae, etc.

A multi-assay processing, analysis and/or detection method of the instant disclosure may include any combination of assays including but not limited to e.g., any combination of assays for detecting a target nucleic acid derived from any combination of the organisms described herein.

In some instances, a multi-assay processing, analysis and/or detection method of the instant disclosure may include a combination of assays for detecting two or more target nucleic acid from or derived from HIV, HCV, HBV, CT/NG (*Chlamydia trachomatis* (CT)/*Neisseria gonorrhoeae* (NG)) and HPV.

In some instances, a multi-assay processing, analysis and/or detection method of the instant disclosure may include a combination of assays for detecting two or more target nucleic acid from or derived from CMV, EBV, BK virus, MRSA, C. Diff. (*Clostridium difficile*) and VRE.

In some instances, a multi-assay processing, analysis and/or detection method of the instant disclosure may include a combination of assays for detecting two or more target nucleic acid from or derived from Adenovirus, TB, VZV (Varicella-zoster virus), HSV, JC virus and Enterovirus.

In some instances, a multi-assay processing, analysis and/or detection method of the instant disclosure may include a combination of assays for detecting two or more target nucleic acid from or derived from LGV (*Lymphogranuloma venereum*), one or more viruses of the Respiratory Viral Panel (RVP; Human Metapneumovirus (hMPV), Rhinovirus, Influenza A, Influenza A subtype H1, Influenza A subtype H3, Influenza B, Respiratory Syncytial Virus (RSV) A, Respiratory Syncytial Virus (RSV) B, Parainfluenza Virus 1, Parainfluenza Virus 2, Parainfluenza Virus 3, Adenovirus), HHV6 (human herpesvirus 6), Trich/Myco (*Trichomonas* (Trich)/*Mycoplasma* (Myco)) and Norovirus.

In some instances, a multi-assay processing, analysis and/or detection method of the instant disclosure may include a combination of assays for detecting two or more target nucleic acid from or derived from HIV, HCV, HBV, CT/NG, HPV, CMV, EBV, BK, MRSA, C. Diff. VRE, Adenovirus, TB, VZV, HSV, JC, Enterovirus, LGV, RVP, HHV6, Trich/Myco and Norovirus.

In some embodiments, the methods of the instant disclosure include processing multiple assays according to the longest processing and/or analysis step required for each particular assay. For example, in some instances, a multi-assay processing method may include preparing a sample processing unit (SPU) cartridge for a period of time corresponding to the longest SPU cartridge preparation step required for all of the assays of the plurality. An SPU cartridge preparation step, as described herein, may include the aliquoting of necessary reagents into sample processing wells of a multi-well vessel in preparation for sample processing, e.g., lysis and extraction of nucleic acids. SPU cartridge preparation steps for different assays will vary, e.g., because certain assays may require more or less reagents than another assay.

In some instances, a multi-assay processing method may include a sample loading step that is performed for a period of time corresponding to the longest sample loading step required for all of the assays of the plurality. A sample loading step, as described herein, may include the loading of the sample into the SPU cartridge of a particular assay. Sample loading steps may vary, e.g., because a particular assay may require more or less sample than another assay.

In some instances, a multi-assay processing method may include a sample processing step (e.g., as performed by a SPU module) that is performed for a period of time corresponding to the longest sample processing step required for all of the assays of the plurality. Sample processing steps include but are not limited to sample lysis (including the chemical, physical and/or temporal components thereof), washing steps (including but not limited to one or more washing steps including one washing step, two washing steps, three washing steps, etc.), nucleic acid elution, etc. The length of sample processing steps for different assays will vary for numerous reasons including but not limited to e.g., because a longer or shorter lysis time may be required for a particular organism or cell from which nucleic acid is to be extracted, because more or less wash steps are required to sufficiently clean the extracted nucleic acid before amplification and detection, because elution times may vary, etc.

In some instances, a multi-assay processing method may include a nucleic acid amplification and analysis step that is performed for a period of time corresponding to the longest nucleic acid amplification and analysis step required for all of the assays of the plurality. Nucleic acid amplification and analysis steps as described herein will generally refer to but are not limited to real-time PCR amplification and analysis steps. The necessary time period required for nucleic acid amplification and analysis for a particular assay will vary for numerous reasons including but not limited to e.g., the likely starting amount of target nucleic acid, the hybridization efficiency of the particular primers of the assay, the length of the amplicon, the amount of amplification required for sufficient detection, etc.

The different steps of a multi-assay processing method may represent atomic operations, where an atomic operation in a multi-assay processing instrument may be allocated a fixed amount of time in a lockstep protocol. Atomic operation length for various steps in an assay (e.g., sample loading steps, sample processing steps, nucleic acid amplification and analysis steps, etc.) may be determined by comparing the length of time required to complete the particular step for each of the various assays and identifying that which requires the longest amount of time across all assays. Accordingly, various steps of a subject lockstep protocol may be referred herein, in some instances, as atomic operations.

In some embodiments, the analysis step of the amplification and analysis step may be standardized across assays. For example, a method of multi-assay analysis (e.g., quantification) may include scanning with an optical detector at a regular interval, e.g., where the interval is set and does not vary either during the amplification or across assays. In such instances, the nucleic acid amplification protocol used may be considered to be a single protocol where the invariant characteristics of the protocol include the scan frequency and the overall length of the amplification. However, other components of the amplification protocol (e.g., the annealing times, the ramp times, the melt times, the annealing temperature, the melt temperature, etc.) need not be fixed and may vary from one assay to another provided common measurement timepoints may be aligned sufficient for quantification of the nucleic acid amplification in each assay.

Common measurement timepoints may be aligned, e.g., by staggering the start (e.g., by delaying the start of a second assay after a first assay has begun) such that the assay protocols align with the optical scanning device at nearly equivalent points in the amplification reaction. For example, in some instances, assay starts may be staggered such that, at the moment the optical scanning device passes, each assay is at a nearly equivalent point in the amplification reaction. The desired nearly equivalent point will vary and may include e.g., the end of the annealing step, the start of a ramp step, etc.

In some instances, the initiation of amplification protocols in spaced reaction vessels need not be staggered. For example, in some instances, the scan speed of a analysis unit is sufficiently fast such that amplification protocols initiated at the same time but performed in reaction vessels some distance apart can be scanned in sufficiently rapid succession to produce measurements that are at essentially the same relative time point in the amplification cycle or at least close enough time points in the amplification cycle that they are comparable.

In some instances, a multi-assay processing method may include a rehydrating step that is performed for a period of time corresponding to the longest rehydration step required for all of the assays of the plurality. Rehydration steps include but are not limited to rehydration of lyophilized reagents (including but not limited to e.g., lyophilized buffer, lyophilized primers, lyophilized dNTPs, etc.). The length of rehydration steps for different assays will vary for numerous reasons including but not limited to e.g., the number of reagents to be rehydrated because, for example, different assays may include e.g., different numbers or primers and/or primer pairs, etc.

In some instances, a multi-assay processing method may include a pretreating step that is performed for a period of time corresponding to the longest pretreating step required for all of the assays of the plurality. Pretreating steps include but are not limited to contacting the sample with a protease, e.g., contacting the sample with a protease prior to lysis of the sample. The length of pretreating steps for different assays will vary for numerous reasons including but not limited to e.g., the necessity of pretreatment, the particular pretreatment reagents used (e.g., the particular protease or proteases used), etc.

In some instances, a multi-assay processing method may include an elution step that is performed for a period of time corresponding to the longest elution step required for all of the assays of the plurality. Elution steps include but are not limited to contacting a solid support (e.g., a bead, a particle, a membrane, a filter, etc.) adhered to the nucleic acid from the lysed sample with a solution of buffer sufficient to dissolve and remove the nucleic acid from the solid support. The length of elution steps for different assays will vary for numerous reasons including but not limited to e.g., the amount of nucleic acid expected to be isolated, the physical and/or chemical characteristics of the isolated nucleic acid expected of the sample, the elution buffer used, etc.

In some instances, a multi-assay processing method may include one or more lysis/eluate transfer steps that are performed for period(s) of time corresponding to the longest lysis/eluate transfer step required for all of the assays of the plurality. Lysis/eluate transfer steps include but are not limited to transferring the lysed sample to a separate vessel, transferring the eluate to a separate vessel (e.g., a reaction vessel) and/or any physical movement steps required by a device to achieve such processes. The length of lysis/eluate transfer steps for different assays will vary for numerous reasons including but not limited to e.g., the amount of lysed sample, the amount of eluate, etc.

The methods of multi-assay processing and analysis as described herein provide for simplified programming (e.g., software programming) of an automated multi-assay processing/analysis device by limiting scheduling complexity for steps of the automated processes, including sample processing and analysis. The multi-assay methods allow for the processing and/or analysis of multiple different assays simultaneously. As described herein, corresponding steps of different assays may be allocated the same amount of time, even in instances where the corresponding steps do not require the same amount of time in the plurality of assays. In some instances, the corresponding steps (e.g., bulk filling step, pipetting step, SPU cartridge preparation step, sample addition step, sample processing step, etc.) of different assays may be each allocated a fixed amount of time (e.g., where the fixed amount of time corresponds to the longest period of time required for the particular step out of all the different assays).

In some instances, methods performed using devices of the instant disclosure will eliminate resource contention that results from limiting resources of the device. A device of the instant disclosure may include a limiting resource that is utilized in more than one process of the device such that when parallel batches are processed the resource may, unless precautions are taken, be required for two processes (i.e., one in each parallel batch) simultaneously. Resources of the device for which resource contention is of issue, as described herein, generally include device hardware resources such as e.g., robotic components (e.g., liquid handling (e.g., bulk filling and/or pipetting) robots, vessel (e.g., SPU cartridge and/or reaction vessel) transport robots, sample processing robots, analysis (e.g., data capture) robots, waste transport robots, and the like). System resources that will generally not be of issue in resource contention, as described herein, include e.g., consumable resources, such as e.g., reagents, vessels, etc.

Methods of the instant disclosure eliminate such resource contention by deploying a common lockstep protocol that includes one or more delay points within or between steps of the protocol. For example, in some instances, a method of the instant disclosure may include a common lockstep protocol that includes a delay point within a SPU cartridge preparation step or between a SPU cartridge preparation step and a next step of the protocol. Such a delay point may be appropriate where, e.g., a resource limiting component is utilized in the SPU cartridge preparation step and/or an adjacent step of the protocol.

In some instances, a method of the instant disclosure may include a common lockstep protocol that includes a delay point within a sample loading step or between a sample loading step and a next step of the protocol. Such a delay point may be appropriate where, e.g., a resource limiting component is utilized in the sample loading step and/or an adjacent step of the protocol.

In some instances, a method of the instant disclosure may include a common lockstep protocol that includes a delay point within a sample processing step or between a sample processing step and a next step of the protocol. Such a delay point may be appropriate where, e.g., a resource limiting component is utilized in the sample processing step and/or an adjacent step of the protocol.

In some instances, a method of the instant disclosure may include a common lockstep protocol that includes a delay point within a nucleic acid amplification/analysis step or between a nucleic acid amplification/analysis step and a next step of the protocol. Such a delay point may be appropriate where, e.g., a resource limiting component is utilized in the amplification/analysis step and/or an adjacent step of the protocol.

In some instances, a method of the instant disclosure may include a common lockstep protocol that includes a delay point within a rehydrating step or between a rehydrating step and a next step of the protocol. Such a delay point may be appropriate where, e.g., a resource limiting component is utilized in the rehydrating step and/or an adjacent step of the protocol.

In some instances, a method of the instant disclosure may include a common lockstep protocol that includes a delay point within a pretreating step or between a pretreating step and a next step of the protocol. Such a delay point may be appropriate where, e.g., a resource limiting component is utilized in the pretreating step and/or an adjacent step of the protocol.

In some instances, a method of the instant disclosure may include a common lockstep protocol that includes a delay point within an elution step or between an elution step and a next step of the protocol. Such a delay point may be appropriate where, e.g., a resource limiting component is utilized in the elution step and/or an adjacent step of the protocol.

In some instances, a method of the instant disclosure may include a common lockstep protocol that includes a delay point within one or more lysis/eluate transfer steps or between one or more lysis/eluate transfer steps and a next step of the protocol. Such a delay point may be appropriate where, e.g., a resource limiting component is utilized in the one or more lysis/eluate transfer steps and/or an adjacent step of the protocol.

Figure 5:
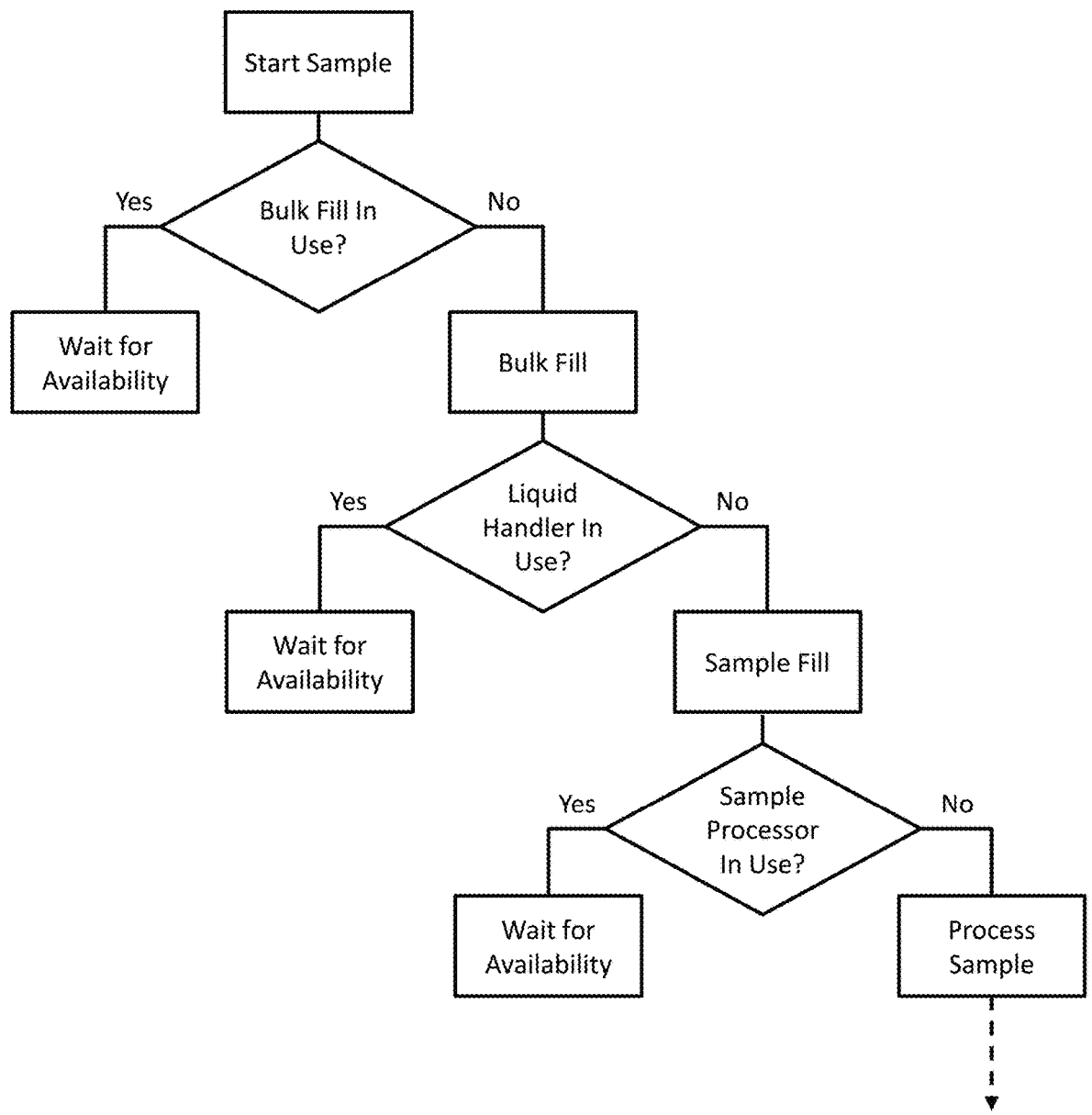
FIG. 5 depicts a flow chart for a conventional sample processing protocol performed in an automated system subject to resource contention.

A conventional sample processing/analysis protocol not employing the methods of the present disclosure but using an automated device that is subject to resource contention is depicted in the decision tree of FIG. 5. As shown, once the sample process is begun, each processing step is preceded by a decision where the device must determine whether a necessary resource for the next step is or is not available. For example, prior to initiating a bulk fill step, the device must determine whether the bulk filling robot is or is not in use. If the bulk filling robot is in use then the device must wait until the bulk filling robot becomes available before proceeding to the bulk fill step. Similarly, prior to performing the sample filling step, the device must determine whether or not the liquid handling robot is or is not in use. If the liquid handling robot is in use then the device must wait until the liquid handling robot is available before proceeding to the sample filling step. The requirement for such decisions continues at each step where a limiting resource is employed. Scheduling complexity in such a system is amplified where many different sample processes are desired and entry of new samples into the system is unpredictable (such as in a clinical laboratory).

Figure 6:
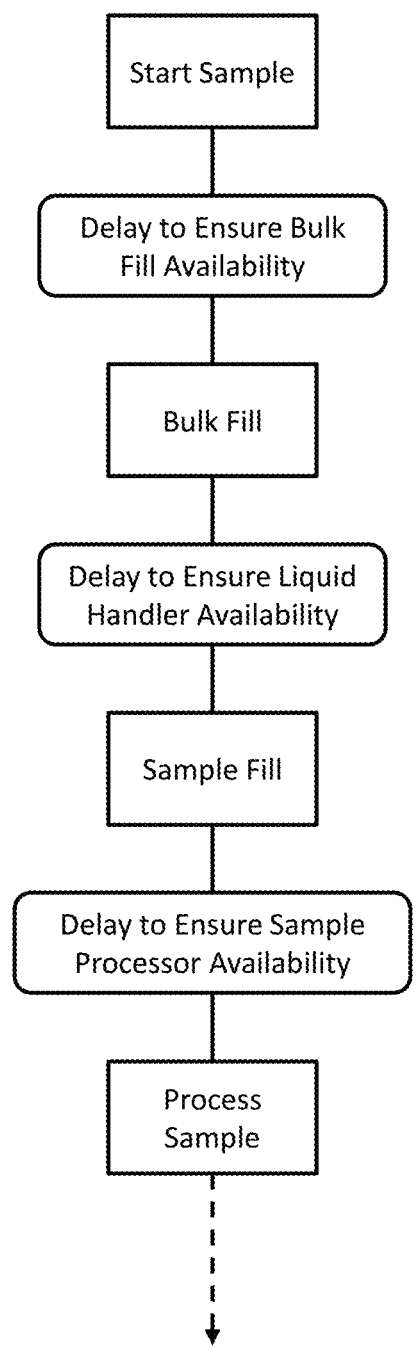
FIG. 6 depicts a flow chart for an embodiment of the present methods employing a lockstep protocol with scheduled delays between process steps.

In embodiments of the present methods employing a lockstep protocol, delays may be configured into the protocol at predetermined and defined positions. For example, as depicted in FIG. 6, predetermined delays are inserted into the protocol before or between individual process steps (i.e., a delay is inserted prior to bulk filling, a delay is inserted between bulk filling and sample filling, a delay is inserted between sample filling and sample processing, etc.). Although depicted before or between steps of the protocol in FIG. 6, such delays may also be inserted within a step. Such delays are not the result of waiting for the availability of a limiting resource but instead specifically designed such that parallel sample processes do not require the same limiting resource at a given time. Unlike waiting for availability of a limiting resource as depicted in FIG. 5, the delays of FIG. 6 are not introduced because a resource needed for the next step is in use. Instead, the delays assure that resource contention does not occur thus eliminating unplanned waiting for the availability of a limiting resource. As such, resource availability (i.e., "in use") decisions are not required. Although the example depicted in FIG. 6 presents a delay between each step, such is not necessarily required as the number of delays present in a lockstep protocol of the present methods may, as described above, vary in presence/absence, number, frequency and length.

Idealized lockstep methods (i.e., lockstep methods that do not take resource contention into account or lockstep methods performed on devices configured with no limiting resources) may be modified to include a delay step where the method is employed on a device with limiting resources. Such devices include those having one or more limiting components, including of those components described herein. In some instances a modified lockstep method to eliminate resource contention may be employed on a device having e.g., one robotic pipettor, one bulk filling robot, one waste robot, one cartridge handling robot, or a device having some combination of such limiting resources. Limiting resources are also not limited to devices having only one of a particular resource and may include e.g., those having two, three, four, five, six, seven, eight, nine or even ten or more of a particular resource provided the particular device is configured to process a sufficient number of batches to induce resource contention.

In some instances, the described method may be employed to complete, from start (i.e., initial sample aspiration/preparation) to finish (i.e., data acquisition and storage/transfer), up to 96 operations or greater in a 8 hour period, including but not limited to e.g., 108 operations or greater, 120 operations or greater, 132 operations or greater, 144 operations or greater, 156 operations or greater, 168 operations or greater, 180 operations or greater, 192 operations or greater, 204 operations or greater, 216 operations or greater, 228 operations or greater, 240 operations or greater, 252 operations or greater, 264 operations or greater, 276 operations or greater, 288 operations or greater, 300 operations or greater, etc., where by "operation" is meant an analysis and/or detection method for a particular nucleic acid analyte run parallel with at least one other analysis and/or detection method for a different nucleic acid analyte (e.g., a HIV assay run in parallel with a HCV assay). Such operation throughput may be achieved taking resource contention into account, including e.g., where the subject device includes a single robotic pipettor, a single bulk filling robot, a single waste handling robot, a single SPU cartridge handling robot, and four amplification/analysis units (each holding twelve reaction vessels and a single analysis robot).

In some instances, throughput of up to 288 operations or greater per 8 hour period may be achieved, taking resource contention into account, including e.g., where the subject device includes a single robotic pipettor, a single bulk filling robot, a single waste handling robot, a single SPU cartridge handling robot, and four amplification/analysis units (each holding twelve reaction vessels and a single analysis robot), where an operation includes an analysis and/or detection method for a particular nucleic acid analyte run parallel with at least two other analysis and/or detection methods for different nucleic acid analytes.

Furthermore, an ordinary skilled artisan will readily understand that the addition of particular limiting resources to a device for which a common lockstep protocol has been designed to eliminate resource contention may allow for modification of the common lockstep protocol, e.g., to decrease the cadence. For example, where a particular resource is limiting and a common lockstep protocol is configured to eliminate contention of the resource, when a duplicate of the limiting resource is added to the device the common lockstep protocol may be modified, e.g., by the removal of one or more delay steps, to shorten the cadence as compared to the initial common lockstep protocol. Accordingly, the instant disclosure encompasses common lockstep protocols derived by decreasing resource limitation of a device and modifying the common lockstep protocol, including e.g., where the modification results in a cadence that is modified, e.g., decreased.

Devices and Systems

The instant disclosure provides for devices and systems, e.g., automated multi-assay processing/analysis devices and systems, that function according to the methods as described herein. Such devices and systems will include a plurality of modules that are coordinated, by one or more centralized controllers, to operate the system or device according to the methods as described herein.

In some instances, the methods as described herein find use in a system or one or more components of a system for automated analysis and sample analysis systems as described in U.S. Ser. No. 62/308,617 and U.S. Ser. No. 62/357,772, the disclosures of which are incorporated herein by reference in their entireties.

In some instances, a multi-assay processing/analysis system of the instant disclosure will include a sample processing unit (SPU) cartridge preparation module, a sample loading module, a sample processing module (i.e., a SPU module) and/or a nucleic acid amplification and analysis module. Such systems will generally require control circuitry that is configured with non-transitory programing to operate components of the device or system to perform a method as described herein.

In some instances, the methods as described herein find use in conjunction with a SPU system or component thereof, including but not limited to e.g., a SPU cartridge or one or more parts thereof as described in U.S. Ser. No. 62/308,618, the disclosures of which are incorporated herein by reference in their entireties. In some instances, the methods as described herein also find use in conjunction with a nucleic acid amplification and detection device, system and/or method or a component thereof as described in U.S. Ser. No. 62/308,632, the disclosures of which are incorporated herein by reference in their entireties.

In some instances, a multi-assay processing/analysis system of the instant disclosure will also include a pipette module (e.g., a robotic pipettor) for performing various automated pipetting functions for one or more modules of the device. For example, in some instances a robotic pipettor may be used for rehydrating lyophilized reagents, as part of a SPU cartridge preparation module, as part of a sample loading module, and or a combination thereof. In some instances, separate pipette modules may be used for one or more functions of the method.

In some instances, a multi-assay processing/analysis system of the instant disclosure will also include an SPU configured for pre-treating each sample prior to processing the sample, a liquid transfer module and/or a reaction transfer module.

Multi-assay automated systems of the present disclosure include a SPU module. The SPU module will generally include components necessary for the filling of a SPU cartridge, where an SPU cartridge may be a multi-well device that contains all or nearly all of the reagents necessary for the processing of an assay as described herein. In other instances, an SPU module may rely on another component of the system, e.g., the pipette module for SPU cartridge filling. SPU modules may further include components for sample processing including but not limited to e.g., components for the pretreatment of samples, components for the chemical, enzymatic and/or mechanical lysis of samples, components for the washing of samples and/or sample analytes, components for the elution of nucleic acid analytes, etc.

SPU cartridges may be prepared in a SPU cartridge preparation position. The preparation may include one or more (e.g., 2 or more) SPU cartridge preparation positions, where SPU cartridges are transported to the one or more SPU cartridge preparation positions by a robotic SPU cartridge handler. Depending on the particular configuration of the system, the SPU cartridges transported to the preparation positions may be empty or may include samples (e.g., omitting the need for a sample transfer step). In some instances, a SPU cartridge may include most if not all of the reagents necessary for the sample preparation process (e.g., eliminating the need for further setup steps of the SPU cartridge).

Sample loading modules of the subject disclosure include a liquid handling robot (e.g., a robotic pipettor) configured to aspirate all or a portion of a sample and dispense it into a SPU cartridge according to instructions received from programming. Accordingly, sample loading module may be controlled by circuitry configured to control module components of a multi-assay system according to the methods described herein.

Sample processing modules of the subject disclosure include devices for the physical manipulations of samples required to isolate nucleic acid from the sample. For example, in some instances, a sample processing module may include a plunger for physical agitation of the sample to promote lysis. A sample processing module may also include a magnetize-able rod for use in manipulating magnetic beads or other magnetic solid support for nucleic acid of the sample. For example, in some instances, following lysis in the sample processing module, magnetic beads or particles may be used to bind nucleic acid and the magnetic beads or particles may be extracted, carrying the nucleic acid, using a magnetize-able rod. In some instances, the plunger may serve as the magnetize-able rod, e.g., through insertion of a magnet into the plunger. The same processing module may further include mechanisms for transferring nucleic acid between wash wells, including e.g., where the magnetize-able rod or a magnetize-able plunger serves such a purpose. In addition, the sample processing module may further be configured to allow for the elution of nucleic acid from a bound solid support, such as magnetic beads.

Accordingly, the sample processing module may perform a variety of sample processing functions and will include the necessary components for serving such functions. As such, the individual functions of the sample processing unit (i.e., physical manipulations, lysis, elution, etc.) may be coordinated into a multi-assay protocol as described herein where, e.g., the length of any one particular step may be increased for a particular assay to match the time required for the step for the assay in which the particular step takes the longest. In some instances, only the overall length of the sample processing step will be coordinated in a multi-assay protocol including e.g., the sub-steps of sample processing (i.e., physical manipulations, lysis, elution, etc.) may not be coordinated.

In some instances, the methods as described herein may be applied to or used in conjunction with a sample processing device and/or a sample processing method as described in U.S. Ser. No. 62/308,645, the disclosures of which are incorporated herein by reference in their entireties.

Nucleic acid amplification and analysis modules of the instant disclosure will generally include the components of a thermocycler and an optical detection system. Where electricity is employed to control thermal cycling, at a minimum, a thermocycler useful in nucleic acid amplification with include a thermal block, a thermoelectric cooler and a control unit, such components configured together to regulate the temperature of a reaction vessel in a controlled manner so as to cycle the reaction through multiple rounds of heating and cooling through a defined series of temperature steps. A nucleic acid amplification device of the instant disclosure may include thermoregulatory components in addition to the thermal block and thermoelectric cooler including but not limited to e.g., a heatsink, a fan, a duct, a vent, etc. Two or more thermoregulatory components of a nucleic acid amplification device will generally be in thermal contact with one another.

The analysis component of a nucleic acid amplification and analysis module will generally include a multi-reaction analysis devices configured for the analysis of multiple amplification reaction vessels during the amplification reactions. Multi-reaction analysis devices of the instant disclosure allow for the monitoring of multiple real-time PCR reactions. Such multi-reaction analysis devices include optical components, conveyor components and signal detection/ processing components wherein such components are configured for the frequent monitoring of multiple reaction vessels.

Multi-reaction analysis devices of the instant disclosure include optical components sufficient for the optical analysis of nucleic acid amplification reactions, including real-time PCR reactions, as described herein. Such optical components will include illumination components, including one or more excitation components, and components for receiving emission light from the reaction vessel. In certain embodiments a linear conveyer is paired with linearly arranged optical components and linearly arranged reaction vessels to allow for the scanning of the optical components, by means of the conveyor, past the reaction vessels to mediate the analysis. As such, in some instances, control circuitry is configured to regulate the rate and/or interval of scanning of the optical detector to operate the system according to the methods as described herein. In some instances, the scanning internal is invariant and the control circuitry maintains a constant rate and/or interval of scanning. In other instances, the scanning interval is variant.

Systems of the instant disclosure may include various robotic handling components, including but not limited to e.g., a robotic SPU cartridge handler, a liquid handling robot, a bulk filling robot, a waste robot, and the like. Such robotic components may function to distribute SPU cartridges to various locations throughout the system including but not limited to e.g., a bulk filling station, a pipetting station, a sample filling station, a sample processing station, a waste station, etc., according to instructions received from programming. In some instances, systems of the instant disclosure may include a liquid handling robot where such a robot may contain an automated pipetting system for dispensing and/or aspirating liquids according to instructions received from programming. In some instances, a control circuit of the instant disclosure may include programming configured to control the robotic handling components according to the methods described herein. In some instances, a liquid transfer module may include a liquid handing robot configured to dispense and/or aspirate liquid according to instructions received from programming.

Robotic handlers of the instant disclosure are not limited to those configured to relocate SPU cartridges and liquids and may also include e.g., a reaction transfer module configured to transfer a reaction vessel to another location, e.g., to transfer from a sample preparation and/or processing location to an amplification/detection location, according to instructions received from programming. In some instances, components of a liquid handling robot may serve to handle non-liquid components including but not limited to serving as a reaction vessel transfer module.

As described herein, the various components of the multi-assay processing/analysis system may be configured according to a method with a plurality of steps which, although different in length as they proceed, are made the same length across all assays and may include delay periods within and/or between steps to function as a common lockstep protocol for all assays. Such coordinated processing and analysis is made possible by hardware and software programing of control circuitry configured to operate the various system components according to the unified protocol. As such, the advance from one component to another may be pre-timed. However, in certain instances, steps and/or processes may require input, execution or other trigger to proceed and, as such, components of the system may be in electrical communication with one another.

In some instances, the components of the systems as described herein may be connected by a wired data connection. Any suitable and appropriate wired data connection may find use in connecting the components of the described systems, e.g., as described herein, including but not limited to e.g., commercially available cables such as a USB cable, a coaxial cable, a serial cable, a C2G or Cat2 cable, a Cat5/Cat5e/Cat6/Cat6a cable, a Token Ring Cable (Cat4), a VGA cable, a HDMI cable, a RCA cable, an optical fiber cable, and the like. In some instances, e.g., where data security is less of a concern, wireless data connections may be employed including but not limited to e.g., radio frequency connections (e.g., PAN/LAN/MAN/WAN wireless networking, UHF radio connections, etc.), an infrared data transmission connection, wireless optical data connections, and the like.

In certain instances, programming as described herein of the systems of the instant disclosure may be stored in a "memory" and/or on computer readable memory. As such, the devices and systems of the instant disclosure may further include a memory that is capable of storing information such that it is accessible and retrievable at a later date by a computer. Any convenient data storage structure may be chosen, based on the means used to access the stored information. In certain aspects, the information may be stored in a "permanent memory" (i.e. memory that is not erased by termination of the electrical supply to a computer or processor) or "non-permanent memory". Computer harddrive, CD-ROM, floppy disk, portable flash drive and DVD are all examples of permanent memory. Random Access Memory (RAM) is an example of non-permanent memory. A file in permanent memory may be editable and re-writable.

Substantially any circuitry can be configured to a functional arrangement within the devices and systems for performing the methods disclosed herein provided the described considerations are followed. However, as described herein, systems employing the instant methods will generally make use of hardware configurations compatible with the disclosed unified processing and analysis protocols.

The hardware architecture of such circuitry, including e.g., a specifically configured computer, is well known by a person skilled in the art, and can comprise hardware components including one or more processors (CPU), a random-access memory (RAM), a read-only memory (ROM), an internal or external data storage medium (e.g., hard disk drive). Such circuitry can also comprise one or more graphic boards for processing and outputting graphical information to display means. The above components can be suitably interconnected via a bus within the circuitry, e.g., inside a specific-use computer. The circuitry can further comprise suitable interfaces for communicating with general-purpose external components such as a monitor, keyboard, mouse, network, etc. In some embodiments, the circuitry can be capable of parallel processing or can be part of a network configured for parallel or distributive computing to increase the processing power for the present methods and programs. In some embodiments, the program code read out from the storage medium can be written into a memory provided in an expanded board inserted in the circuitry, or an expanded unit connected to the circuitry, and a CPU or the like provided in the expanded board or expanded unit can actually perform a part or all of the operations according to the instructions of the programming, so as to accomplish the functions described.

In addition to the components of the devices and systems of the instant disclosure, e.g., as described above, systems of the disclosure may include a number of additional components, such as data output devices, e.g., monitors and/or speakers, data input devices, e.g., interface ports, keyboards, etc., actuatable components, power sources, etc.

Computer Readable Media

The instant disclosure includes computer readable medium, including non-transitory computer readable medium, which stores instructions for methods described herein. Aspects of the instant disclosure include computer readable medium storing instructions that, when executed by a computing device, cause the computing device to perform one or more steps of a method as described herein.

In certain embodiments, instructions in accordance with the methods described herein can be coded onto a computer-readable medium in the form of "programming", where the term "computer readable medium" as used herein refers to any storage or transmission medium that participates in providing instructions and/or data to a computer for execution and/or processing. Examples of storage media include a floppy disk, hard disk, optical disk, magneto-optical disk, CD-ROM, CD-R, magnetic tape, non-volatile memory card, ROM, DVD-ROM, Blue-ray disk, solid state disk, and network attached storage (NAS), whether or not such devices are internal or external to the computer. A file containing information can be "stored" on computer readable medium, where "storing" means recording information such that it is accessible and retrievable at a later date by a computer.

The computer-implemented method described herein can be executed using programming that can be written in one or more of any number of computer programming languages. Such languages include, for example, Java (Sun Microsystems, Inc., Santa Clara, CA), Visual Basic (Microsoft Corp., Redmond, WA), and C++ (AT&T Corp., Bedminster, NJ), as well as any many others.

The following examples are offered by way of illustration and not by way of limitation.

EXAMPLES

Example 1: Generation of a Common Lockstep Sample Processing Protocol

The instant example describes the creation of a single lockstep assay timing protocol that harmonizes the processing for each type of assay into a common assay timing protocol where all assays result in the same time and throughput regardless of which assay or mix of assays are being run on the automated device.

The pipetting step, SPU cartridge setup step, sample addition step, pretreatment step, digestion transfer step, SPU processing step, eluate transfer step and amplification/detection step was determined for various assays including HIV, HCV, CT/NG and HBV. The longest of each step (i.e., the longest pipetting step, the longest SPU cartridge setup step, the longest sample addition step, the longest pretreatment step, the longest digestion transfer step, the longest SPU processing step, the longest eluate transfer step and the longest amplification/detection step) for each assay were compiled into a single common idealized "lockstep" protocol. FIG. 1 provides an example of how an idealized common lockstep assay timing protocol was derived from several assays (e.g., HIV, HCV, CT/NG and HBV) that have unique processing steps and times.

Figure 2:
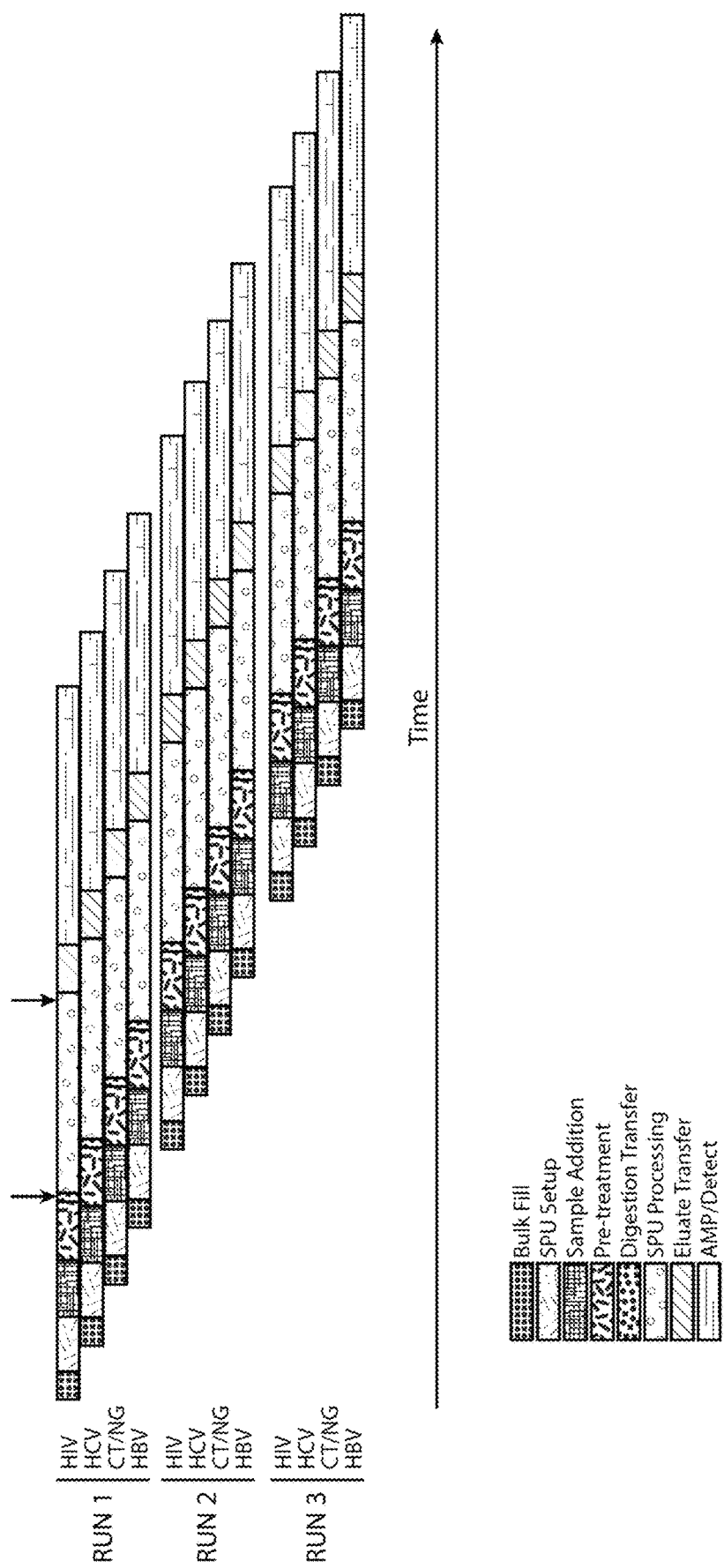
FIG. 2 demonstrates how four different assay types (HIV, HCV, CT/NG and HBV), utilizing a common lockstep assay timing protocol, can be processed over three runs given an idealized system with essentially limitless resources. Resource contention is indicated.

The idealized lockstep timing protocol provided in FIG. 1 does not take into account the limited resources of an actual device (e.g., a device configured to have a single robotic pipettor, a single bulk filling robot, a single waste handling robot, a single SPU cartridge handling robot, etc.). To generate sequences which allow operation on a number of batches within a system simultaneously using limited resources, the idealized lockstep protocol of FIG. 1 was used as a starting point and modified to eliminate resource contention. For example, FIG. 2 illustrates how four different assay types (HIV, HCV, CT/NG and HBV), utilizing an idealized common lockstep assay timing protocol would be processed in an idealized system without considering for resource contention (i.e., if a dedicated resource for all processing steps listed in the table in the figure were present for each batch). However, if SPU setup and sample addition were to use the same resource (e.g., a single robotic pipettor) and/or sample processing and pretreatment were to use the sample resource (e.g., a single robotic pipettor), resource contention would occur (as indicated on FIG. 2 as vertical arrows) and much greater staggering of processing steps would be required.

Rather than simply restricting batch processing to a serial protocol where resource contention is alleviated by preventing the initiation of a new batch until a previous batch is complete, the lockstep protocol was modified to include a sequence of delays inserted between and/or within steps to generate a modified common lockstep protocol having an optimized cadence (i.e., batch per unit time) taking into account all potential assays to be run on the device.

For example, as depicted in FIG. 3, when resources are unlimited ("Unlimited Resource Case") a lockstep protocol may concurrently process successively initiated batches without concern for resource contention. However, when resources are limiting ("Limited Resources with Resource Contention"), e.g., where only three resources are available that perform "step 2", resource contention (as indicated with underlining) occurs between e.g., the third and fourth batches at the initiation of "step two" of the fourth batch because the first batch has yet to complete "step 2" and all three of the available resources are occupied. In the "Limited Resources with Resource Contention" example, further resource contention (also indicated in FIG. 3 with underlining) is seen when assuming that only one resource is available that performs each of "step 1", "step 3" and "step 5".

These resource contentions were eliminated (as shown in the "Contentions Eliminated" panel of FIG. 3) by modeling the actual processing of a resource limited device to identify resource contentions and determine where the addition of delay points ("Delay") would prevent such resource contention and produce an optimized cadence.

This common lockstep protocol with added delay points allows for the concurrent (simultaneous and/or overlapping) processing/analysis of different assays without affecting throughput and eliminating resource contention. Furthermore, the lockstep protocol allows initiation of an additional different assay or a new batch of an already running assay during the processing of a previously started assay without affecting the processing of either assay.

The lockstep protocol further simplifies automated device programming (e.g., software) and operation. However, the hardware functioning in an automated device operating under a lockstep protocol required additional design considerations.

In one tested embodiment, the hardware allowed for 12 different assays (each in batches of 4 samples each) to be run at any one time on a single device without resource contention even where resources are limiting (e.g., where the device has a single robotic pipettor, a single bulk filling robot, a single waste handling robot and a single SPU cartridge handling robot). Batch sizes of 4 samples allows for different assay attributes per grouping of 4 samples, as long as the overall processing time is the same for all batches (i.e., all batches conform to the overall common lockstep protocol length). For example, in sample preparation, each group of 4 samples can have a different temperature control but this will not impact the overall processing time.

The described example of a common lockstep assay timing protocol simplified the software scheduling complexity for an automated instrument that processes multiple different assays simultaneously (i.e., in parallel) since each processing step/resource in the system (i.e. Pipetting, SPU Cartridge Setup, Sample Addition, etc.) was allocated a fixed amount that included the time necessary to complete the step in the most resource intensive assay and additional added delay to align the step into an optimized cadence that eliminates contention for shared resources.

Furthermore, for the amplification and detection subsystem in this embodiment, independent thermal control was provided for each set of two samples. The system used this advanced control to delay the protocol start for each subsequent pair of samples in order to read all samples at common measurement time points (e.g., as close to the same relative time in each protocol as possible).

Figure 4:
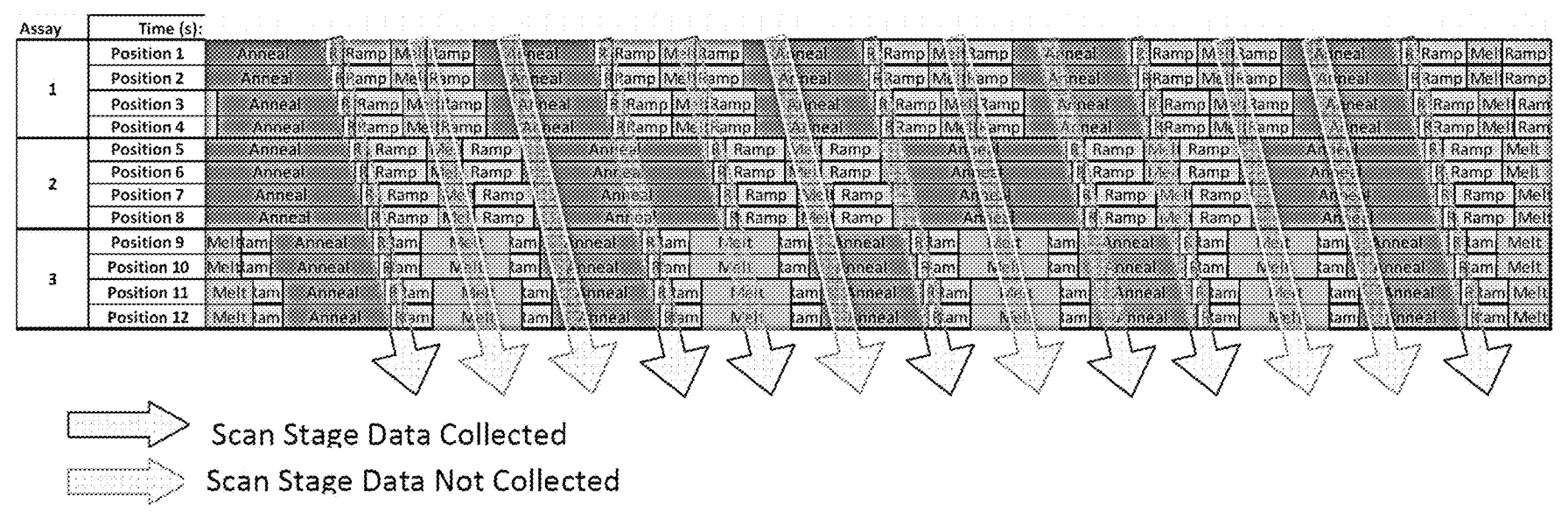

The protocols were structured such that the amplification and detection for each assay fit within a common optical protocol (i.e., scanning protocol) such that the scan stage can reach each assay at the correct time to make a measurement. In the described example, the scan stage continuously scans all assays (with the option for pauses or calibration steps between scans) and particular data for each assay was captured when relevant. FIG. 4 provides an example for such coordinated scanning in three different assays (each with a pair of reaction vessels). The arrows and steps indicate when each assay requires a scan to occur. As can be seen, all three assays do not always align and only the relevant data for each assay need be written to the output file and/or used in further measurement and analysis.

The common lockstep operation significantly simplified the software scheduling complexity for the tested instrument overall. By having a common lockstep protocol, the software followed a deterministic model of when different activities needed to occur for different resources. In the event that a step completes early, the system is programed to wait until the period was over to proceed forward with that step. This structured scheduling ensured that there are not resource contentions.

Notwithstanding the appended claims, the disclosure is also defined by the following clauses:

1. A method of multi-assay processing, the method comprising:
   a) preparing a sample processing unit (SPU) cartridge for each of two or more different target nucleic acid detection assays;
   b) loading a sample into each prepared SPU cartridge;
   c) processing each loaded SPU cartridge to isolate a sample nucleic acid for each of the two or more different target nucleic acid detection assays; and
   d) amplifying and analyzing each sample nucleic acid for a target nucleic acid specific to each of the two or more different target nucleic acid detection assays, wherein the method comprises at least one delay step within or between steps a) through d) and steps a) through d) are each performed for a time period that is equal for the two or more different target nucleic acid detection assays.

2. The method according to clause 1, wherein the method comprises a delay step between steps a) and b).

3. The method according to any one of clauses 1-2, wherein the method comprises a delay step between steps b) and c).

4. The method according to any one of clauses 1-3, wherein the method comprises a delay step between steps c) and d).

5. The method according to any one of clauses 1-4, wherein the method further comprises rehydrating lyophilized reagents for each of the two or more different target nucleic acid detection assays prior to the preparing, wherein the rehydrating is performed for a time period that is equal for the two or more different target nucleic acid detection assays.

6. The method according to clause 5, wherein the method comprises a delay step following the rehydrating.

7. The method according to any one of clauses 1-6, wherein the method further comprises pre-treating each loaded SPU cartridge prior to the processing, wherein the pre-treating is performed for a time period that is equal for the two or more different target nucleic acid detection assays.

8. The method according to clause 7, wherein the method comprises a delay step following the pre-treating.

9. The method according to clause 7, wherein the pre-treating comprises contacting the sample with a protease.

10. The method according to any one of clauses 1-9, wherein the processing comprises transferring the sample into a solution comprising a lysis buffer, wherein the transferring is performed for a time period that is equal for the two or more different target nucleic acid detection assays.

11. The method according to clause 10, wherein the method comprises a delay step following the transferring.

12. The method according to any one of clauses 1-11, wherein the processing comprises eluting the nucleic acid and transferring the eluted nucleic acid into a reaction vessel for the amplifying and analyzing, wherein the eluting is performed for a time period that is equal for the two or more different target nucleic acid detection assays.

13. The method according to clause 12, wherein the method comprises a delay step following the eluting.

14. The method according to any one of clauses 1-13, wherein the two or more different target nucleic acid detection assays comprises an assay to detect a human immunodeficiency virus (HIV) nucleic acid.

15. The method according to any one of clauses 1-14, wherein the two or more different target nucleic acid detection assays comprises an assay to detect a hepatitis C virus (HCV) nucleic acid.

16. The method according to any one of clauses 1-15, wherein the two or more different target nucleic acid detection assays comprises an assay to detect a hepatitis B virus (HBV) nucleic acid.

17. The method according to any one of clauses 1-16, wherein the two or more different target nucleic acid detection assays comprises an assay to detect a *Chlamydia trachomatis* (CT) nucleic acid, a *Neisseria gonorrhoeae* (NG) nucleic acid or a combination there of.

18. The method according to any one of clauses 1-17, wherein the two or more different target nucleic acid detection assays comprises an assay to detect a Human papillomavirus (HPV) nucleic acid.

19. The method according to any one of clauses 1-18, wherein the two or more different target nucleic acid detection assays comprises an assay to detect a Cytomegalovirus (CMV) nucleic acid.

20. The method according to any one of clauses 1-19, wherein the two or more different target nucleic acid detection assays comprises an assay to detect an Epstein-Barr virus (EBV) nucleic acid.

21. The method according to any one of clauses 1-20, wherein the two or more different target nucleic acid detection assays comprises an assay to detect a BK virus nucleic acid.

22. The method according to any one of clauses 1-21, wherein the two or more different target nucleic acid detection assays comprises an assay to detect a Methicillin-resistant *Staphylococcus aureus* (MRSA) nucleic acid.

23. The method according to any one of clauses 1-22, wherein the two or more different target nucleic acid detection assays comprises an assay to detect a *Clostridium difficile* (D. Diff.) nucleic acid.

24. The method according to any one of clauses 1-23, wherein the two or more different target nucleic acid detection assays comprises an assay to detect a Vancomycin-resistant *Enterococcus* (VRE) nucleic acid.

25. The method according to any one of clauses 1-24, wherein the two or more different target nucleic acid detection assays comprises an assay to detect an Adenovirus nucleic acid.

26. The method according to any one of clauses 1-25, wherein the two or more different target nucleic acid detection assays comprises an assay to detect a tuberculosis (TB) nucleic acid.

27. The method according to any one of clauses 1-26, wherein the two or more different target nucleic acid detection assays comprises an assay to detect a Varicella-zoster virus (VZV) nucleic acid.

28. The method according to any one of clauses 1-27, wherein the two or more different target nucleic acid detection assays comprises an assay to detect a Herpes simplex virus (HSV) nucleic acid.

29. The method according to any one of clauses 1-28, wherein the two or more different target nucleic acid detection assays comprises an assay to detect a JC virus nucleic acid.

30. The method according to any one of clauses 1-29, wherein the two or more different target nucleic acid detection assays comprises an assay to detect an Enterovirus nucleic acid.

31. The method according to any one of clauses 1-30, wherein the two or more different target nucleic acid detection assays comprises an assay to detect a *Lymphogranuloma venereum* (LGV) nucleic acid.

32. The method according to any one of clauses 1-31, wherein the two or more different target nucleic acid detection assays comprises an assay to detect a Respiratory Viral Panel (RVP) nucleic acid.

33. The method according to any one of clauses 1-32, wherein the two or more different target nucleic acid detection assays comprises an assay to detect a human herpesvirus 6 (HHV6) nucleic acid.

34. The method according to any one of clauses 1-33, wherein the two or more different target nucleic acid detection assays comprises an assay to detect a *Trichomonas* (Trich) nucleic acid, a *Mycoplasma* (Myco) nucleic acid or a combination thereof.

35. The method according to any one of clauses 1-34, wherein the two or more different target nucleic acid detection assays comprises an assay to detect a Norovirus nucleic acid.

36. The method according to any one of clauses 1-35, wherein the method process 3 or more different target nucleic acid detection assays.

37. The method according to clause 36, wherein the method process 10 or more different target nucleic acid detection assays.

38. A method of multi-assay quantification, the method comprising:
a) initiating a nucleic acid amplification protocol in a first sample pair;
b) scanning the first sample pair with an optical detector at a regular interval during the nucleic acid amplification protocol, wherein the interval allows for the collection of data by the optical detector at timepoints of the amplification protocol sufficient for quantification of the nucleic acid amplification in the first sample pair;
c) initiating the nucleic acid amplification protocol in a second sample pair at a time that allows the second sample pair to be scanned by the optical detector at the regular intervals and collection of data by the optical detector at timepoints of the amplification protocol sufficient for quantification of nucleic acid amplification in the second sample pair.

39. The method according to clause 38, wherein the initiating of the nucleic acid amplification protocol of the first sample pair and the initiating of the nucleic acid amplification protocol of the second sample pair occur at essentially the same time.

40. The method according to clause 38, wherein the initiating of the nucleic acid amplification protocol of the first sample pair and the initiating of the nucleic acid amplification protocol of the second sample pair occur at different times.

41. The method according to any one of clauses 38-40, wherein the scanning is performed three or more times during the nucleic acid amplification protocol.

42. The method according to any one of clauses 38-41, wherein the interval allows for the collection of data by the optical detector at more timepoints of the amplification protocol than necessary for quantification of the nucleic acid amplification in the first and second sample pairs.

43. The method according to any one of clauses 38-42, wherein the method further comprises initiating the nucleic acid amplification protocol in a third sample pair at a time that allows the third pair to be scanned by the optical detector at the regular intervals and collection of data by the optical detector at timepoints of the amplification protocol sufficient for quantification of nucleic acid amplification in the third sample pair.

44. The method according to clause 43, wherein the initiating of the nucleic acid amplification protocol of the first, second and third sample pairs occur at essentially the same time.

45. The method according to clause 43, wherein the initiating of the nucleic acid amplification protocol of the first, second and third sample pairs occur at different times.

46. The method according to any one of clauses 38-45, wherein the method further comprises initiating the nucleic acid amplification protocol in a fourth sample pair at a time that allows the fourth pair to be scanned by the optical detector at the regular intervals and collection of data by the optical detector at timepoints of the amplification protocol sufficient for quantification of nucleic acid amplification in the fourth sample pair.

47. The method according to clause 46, wherein the initiating of the nucleic acid amplification protocol of the first, second, third and fourth sample pairs occur at essentially the same time.

48. The method according to clause 46, wherein the initiating of the nucleic acid amplification protocol of the first, second, third and fourth sample pairs occur at different times.

49. The method according to any one of clauses 38-48, wherein the method further comprises initiating the nucleic acid amplification protocol in a fifth sample pair at a time that allows the fifth pair to be scanned by the optical detector at the regular intervals and collection of data by the optical detector at timepoints of the amplification protocol sufficient for quantification of nucleic acid amplification in the fifth sample pair.

50. The method according to clause 49, wherein the initiating of the nucleic acid amplification protocol of the first, second, third, fourth and fifth sample pairs occur at essentially the same time.

51. The method according to clause 49, wherein the initiating of the nucleic acid amplification protocol of the first, second, third, fourth and fifth sample pairs occur at different times.

52. The method according to any one of clauses 38-51, wherein the method further comprises initiating the nucleic acid amplification protocol in a sixth sample pair at a time that allows the sixth pair to be scanned by the optical detector at the regular intervals and collection of data by the optical detector at timepoints of the amplification protocol sufficient for quantification of nucleic acid amplification in the sixth sample pair.

53. The method according to clause 52, wherein the initiating of the nucleic acid amplification protocol of the first, second, third, fourth, fifth and sixth sample pairs occur at essentially the same time.

54. The method according to clause 52, wherein the initiating of the nucleic acid amplification protocol of the first, second, third, fourth, fifth and sixth sample pairs occur at different times.

55. A multi-assay processing system, the system comprising:
   a) a sample processing unit (SPU) cartridge preparation module;
   b) a sample loading module;
   c) a SPU processing module;
   d) a nucleic acid amplification and analysis module; and
   e) control circuitry configured to perform the method according to any one of clauses 1-54.

56. The system according to clauses 55, wherein the system further comprises a module for rehydrating lyophilized reagents.

57. The system according to any one of clauses 55-56, wherein the SPU processing module is further configured for pre-treating each sample prior to processing the sample.

58. The system according to any one of clauses 55-57, wherein the system further comprises a reaction transfer module.

59. The system according to any one of clauses 55-58, wherein the system comprises a single robotic pipette resource that functions in the SPU cartridge preparation module.

60. The system according to clause 59, wherein the single robotic pipette resource also functions in the sample loading module.

61. The system according to any one of clauses 59-60, wherein the single robotic pipette resource also functions in the module for rehydrating lyophilized reagents.

62. The system according to any one of clauses 59-61, wherein the single robotic pipette resource also functions in the reaction transfer module.

63. The system according to any one of clauses 55-62, wherein the system further comprises one or more bulk filling robots.

64. The system according to clause 63, wherein the system comprises a single bulk filling robot.

65. The system according to any one of clauses 55-64, wherein the system further comprises one or more waste robots.

66. The system according to clause 65, wherein the system comprises a single waste robot.

67. The system according to any one of clauses 55-66, wherein the system further comprises one or more SPU cartridge handling robots.

68. The system according to clause 65, wherein the system comprises a single SPU cartridge handling robot.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method for performing two or more assays on two or more samples, the method comprising:
   a) loading the two or more samples into a multi-assay processing system for parallel processing of the two or more assays on the two or more samples, the system comprising: a multi-assay processor module, a processor, and a non-transitory computer readable medium programmed with instructions that, when executed by the processor, cause the multi-assay processing system to:
      i) analyze the time schedule for two or more assays that have two or more steps that utilize two or more resources of the multi-assay processing module, wherein the two or more assays have different time durations for one or more of the two or more steps;

ii) determine, before the initiation of the multi-assay processing, introduction of at least one delay step within or between the two or more steps of the two or more assays such that simultaneous processing of the two or more assays does not require, at a given time, the same limiting resource from the multi-assay processing module; and iii) introduce the at least one delay step within or between the two or more steps of the two or more assays in a manner that eliminates resource contention between the two or more resources of the multi-assay processing module thereby allowing parallel processing of the two or more assays in the multi-assay processing module; and b) initiating the multi-assay processing of the two or more samples in the multi-assay processing system.

2. The method of claim 1, wherein the non-transitory computer readable medium is programmed with instructions that, when executed by the processor, cause the multi-assay processing module to allow parallel processing of three or more assays that have three or more steps that utilize three or more resources of the multi-assay processing module.

3. The method of claim 1, wherein each of the two or more assays is nucleic acid detection assay.

4. The method of claim 3, wherein each of the two or more nucleic acid detection assays comprise two or more steps selected from: a) preparing a nucleic acid sample, b) loading the prepared nucleic acid sample, c) amplifying and analyzing the nucleic acid sample.

5. The method of claim 4, wherein the non-transitory computer readable medium is programmed with instructions that, when executed by the processor, cause the multi-assay processing system to introduce the at least one delay step within or between i) steps a) and b); ii) steps b) and c); iii) or a combination of i) and iii), in a manner that eliminates resource contention between the three or more resources of the multi-assay processing module thereby allowing parallel processing of the three or more assays in the multi-assay processing module.

6. The method of claim 3, wherein one of the two or more different target nucleic acid detection assays is an assay to detect a human immunodeficiency virus (HIV) nucleic acid.

7. The method of claim 3, wherein one of the two or more different target nucleic acid detection assays is an assay to detect a human hepatitis C virus (HCV) nucleic acid.

8. The method of claim 3, wherein one of the two or more different target nucleic acid detection assays is an assay to detect a human hepatitis B virus (HBV) nucleic acid.

9. The method of claim 3, wherein one of the two or more different target nucleic acid detection assays detects a human papillomavirus (HPV) nucleic acid.

10. The method of claim 3, wherein one of the two or more different target nucleic acid detection assays is an assay to detect a Cytomegalovirus (CMV) nucleic acid.

11. The method of claim 3, wherein one of the two or more different target nucleic acid detection assays is an assay to detect an Epstein-Barr virus (EBV) nucleic acid.

12. The method of claim 3, wherein one of the two or more different target nucleic acid detection is an assay to detect detects a BK nucleic acid.

13. The method of claim 3, wherein one of the two or more different target nucleic acid detection assays is an assay to detect a Methicillin-resistant *Staphylococcus aureus* (MRSA) nucleic acid.

14. The method of claim 3, wherein one of the two or more different target nucleic acid detection assays is an assay to detect a *Clostridium difficile* nucleic acid.

15. The method of claim 3, wherein one of the two or more different target nucleic acid detection assays is an assay to detect a Vancomycin-resistant *Enterococcus* (VRE) nucleic acid.

16. The method of claim 3, wherein one of the two or more different target nucleic acid detection assays is an assay to detect an Adenovirus nucleic acid.

17. The method of claim 3, wherein one of the two or more different target nucleic acid detection assays is an assay to detect a tuberculosis (TB) nucleic acid.

18. The method of claim 3, wherein one of the two or more different target nucleic acid detection assays is an assay to detect a Varicella-zoster virus (VZV) nucleic acid.

19. The method of claim 3, wherein one of the two or more different target nucleic acid detection assays is an assay to detect a Herpes simplex virus (HSV) nucleic acid.

20. The method of claim 3, wherein one of the two or more different target nucleic acid detection assays is an assay to detect a JC virus nucleic acid.

21. The method of claim 3, wherein one of the two or more different target nucleic acid detection assays is an assay to detect an Enterovirus nucleic acid.

22. The method of claim 3, wherein one of the two or more different target nucleic acid detection assays is an assay to detect a *Lymphogranuloma venereum* (LGV) nucleic acid.

23. The method of claim 3, wherein one of the two or more different target nucleic acid detection assays is an assay to detect a Respiratory Viral Panel (RVP) nucleic acid.

24. The method of claim 3, wherein one of the two or more different target nucleic acid detection assays detects a human herpesvirus 6 (HHV6) nucleic acid.

25. The method of claim 3, the two or more different target nucleic acid detection assays comprises an assay to a *Trichomonas* (Trich) nucleic acid, an assay to detect *Mycoplasma* (Myco) nucleic acid, or an assay to detect the combination of Trich nucleic acid and Myco nucleic acid.

26. The method of claim 3, wherein the two or more different target nucleic acid detection assays comprises an assay to detect a *Chlamydia trachomatis* (CT) nucleic acid, an assay to detect a *Neisseria gonorrhoeae* (NG) nucleic acid, or an assay to detect a combination there of CT nucleic acid and NG nucleic acid.

27. The method of claim 3, wherein the non-transitory computer readable medium is programmed with instructions that, when executed by the processor, cause the multi-assay processing module to allow parallel processing of ten or more assays that have three or more steps that utilize three or more resources in the multi-assay processing module.

28. The method of claim 3, comprising, initiating essentially at the same time, the multi-assay processing of the two or more samples in the multi-assay processing system.

* * * * *

UNITED STATES PATENT AND TRADEMARK OFFICE
CERTIFICATE OF CORRECTION

PATENT NO. : 12,241,131 B2
APPLICATION NO. : 17/390591
DATED : March 4, 2025
INVENTOR(S) : Frank Pawlowski et al.

Page 1 of 1

It is certified that error appears in the above-identified patent and that said Letters Patent is hereby corrected as shown below:

In the Specification

In Column 4, Lines 39-44, delete "In some instances, aspects of the system include one or more waste robots. In some instances, aspects of the system include a single waste robot. In some instances, aspects of the system include one or more SPU cartridge handling robots. In some instances, aspects of the system include a single SPU cartridge handling robot." and insert the same on Column 4, Line 38, as a continuation of the same paragraph.

In Column 10, Line 47, delete "jiroveci," and insert -- jirovecii, --.

In Column 11, Line 41, delete "B. microfti," and insert -- B. microti, --.

In Column 12, Line 10, delete "mekongi-," and insert -- mekongi, --.

In Column 19, Line 24, delete "and or" and insert -- and/or --.

In Column 29, Line 52, delete "clauses" and insert -- clause --.

In the Claims

In Column 31, Line 59, in Claim 12, after "detection" insert -- assays --.

Signed and Sealed this
Third Day of June, 2025

Coke Morgan Stewart
*Acting Director of the United States Patent and Trademark Office*